United States Patent
Li et al.

(10) Patent No.: US 9,199,912 B2
(45) Date of Patent: Dec. 1, 2015

(54) POLYMORPHS OF 4-[2-DIMETHYLAMINO-1-(1-HYDROXYCYCLOHEXYL)ETHYL]PHENYL 4-METHYLBENZOATE HYDROCHLORIDE, METHODS OF PREPARING THE SAME AND USE OF THE SAME

(71) Applicant: Shandong Luye Pharmaceutical Co., Ltd., Yantai, Shangdong (CN)

(72) Inventors: Youxin Li, Langenfeld (DE); Wanhui Liu, Shandong (CN); Yang Lv, Beijing (CN); Guanhua Du, Beijing (CN); Qingguo Meng, Shandong (CN); Mina Yang, Shandong (CN); Fengmei Zhou, Shandong (CN); Ju Li, Shangdong (CN); Xuemei Zhang, Shandong (CN)

(73) Assignees: SHANDONG LUYE PHARMACEUTICAL CO., LTD., Yantai (CN); Youxin Li, Langenfield (DE)

( * ) Notice: Subject to any disclaimer, the term of this patent is extended or adjusted under 35 U.S.C. 154(b) by 0 days.

(21) Appl. No.: 14/259,964

(22) Filed: Apr. 23, 2014

(65) Prior Publication Data

US 2014/0235728 A1 Aug. 21, 2014

Related U.S. Application Data

(63) Continuation of application No. 13/846,773, filed on Mar. 18, 2013, now Pat. No. 8,741,952, which is a continuation-in-part of application No. PCT/CN2011/001637, filed on Sep. 28, 2011.

(30) Foreign Application Priority Data

Oct. 1, 2010 (CN) .......................... 2010 1 0503737

(51) Int. Cl.
| | |
|---|---|
| A61K 31/235 | (2006.01) |
| C07C 213/10 | (2006.01) |
| C07C 215/20 | (2006.01) |
| C07C 215/64 | (2006.01) |
| C07C 219/28 | (2006.01) |

(52) U.S. Cl.
CPC ............. *C07C 215/64* (2013.01); *A61K 31/235* (2013.01); *C07C 213/10* (2013.01); *C07C 219/28* (2013.01); *C07B 2200/13* (2013.01); *C07C 215/20* (2013.01)

(58) Field of Classification Search
CPC ............. A61K 31/235; C07B 2200/13; C07C 213/10; C07C 215/64; C07C 219/28; C07C 69/78; C07C 215/20
See application file for complete search history.

(56) References Cited

U.S. PATENT DOCUMENTS

| | | | |
|---|---|---|---|
| 4,535,186 | A | 8/1985 | Husbands et al. |
| 6,673,838 | B2 | 1/2004 | Hadfield et al. |
| 2003/0158253 | A1 | 8/2003 | Yardley et al. |
| 2003/0191347 | A1 | 10/2003 | Keltjens et al. |
| 2004/0147601 | A1 | 7/2004 | Yardley et al. |
| 2004/0176468 | A1 | 9/2004 | Yardley et al. |
| 2009/0118368 | A1 | 5/2009 | Zhang |

FOREIGN PATENT DOCUMENTS

| | | | |
|---|---|---|---|
| CN | 1706813 | A | 12/2005 |
| CN | 1955159 | A | 5/2007 |
| CN | 100455560 | C | 1/2009 |

*Primary Examiner* — Sarah Pihonak
(74) *Attorney, Agent, or Firm* — Seed IP Law Group PLLC

(57) ABSTRACT

The present disclosure relates to polymorphs of 4-[2-dimethylamino-1-(1-hydroxycyclohexyl)ethyl]phenyl 4-methylbenzoate hydrochloride, methods for preparing the same and use of the same.

8 Claims, 16 Drawing Sheets

POLYMORPHS OF 4-[2-DIMETHYLAMINO-1-(1-HYDROXYCYCLOHEXYL)ETHYL]PHENYL 4-METHYLBENZOATE HYDROCHLORIDE, METHODS OF PREPARING THE SAME AND USE OF THE SAME

CROSS-REFERENCE TO RELATED APPLICATIONS

This application is a continuation of U.S. application Ser. No. 13/846,773, filed Mar. 18, 2013 (now allowed), which is a continuation-in-part application of International Application No. PCT/CN2011/001637, filed Sep. 28, 2011, which claims priority to Chinese Application No. 201010503737.7, filed Oct. 1, 2010, which applications are incorporated herein by reference in their entireties.

BACKGROUND

1. Technical Field

The present disclosure relates to polymorphs of 4-[2-dimethylamino-1-(1-hydroxycyclohexyl)ethyl]phenyl 4-methylbenzoate hydrochloride, methods for preparing the same and use of the same.

2. Description of the Related Art

It is reported that venlafaxine of formula (II), 1-[2-dimethylamino-1-(4-methoxylphenyl)ethyl]cyclohexanol, is a reuptake inhibitor of 5-hydroxytryptamine (5-HT) and norepinephrine (NA), and is widely used for inhibiting reuptake of 5-hydroxytryptamine (5-HT) and norepinephrine (NA) and treating or adjuvantly treating central nervous system diseases such as depression. Venlafaxine is metabolized in liver to form a strongly active metabolite of formula (III), 1-[2-dimethylamino-1-(4-hydroxyphenyl)ethyl]cyclohexanol, a weakly active metabolite of formula (IV), 1-[2-dimethylamino-1-(4-methoxyphenyl)ethyl]cyclohexanol, and a metabolite of formula (V), 1-[2-methylamino-1-(4-hydroxyphenyl)ethyl]cyclohexanol, in which the metabolite (III) and venlafaxine have the same therapeutic effects (see U.S. Pat. No. 4535186A, US20040176468A1, US20040147601A1, US20030191347A1). Moreover, the direct uptake of the metabolite (III) for treating central nervous system diseases, especially, depression, has the advantages of using a single active compound, facilitates the adjustment of dosage and therapeutic effects, alleviates side-effects, and reduces the risk of interaction with other drugs (see U.S. Pat. No. 6673838B2). However, because of the presence of more hydroxyl groups, the metabolite (III) has increased hydrophilicity, thus decreasing absorption rate via oral or transdermal routes of administration and possibly increasing pre-system side effects of unabsorbed drugs. In order to overcome the above defects of the metabolite (III), a series of derivatives represented by formula (VI) were synthesized. These compounds of formula (VI), which are pro-drugs of the metabolite (III), were shown to have metabolized in vivo to produce the metabolite (III), thereby exhibiting therapeutic effects (see Chinese Patent No. CN1955159A, CN1706813A). Chinese Patent No. CN1955159A discloses a compound of formula (I), 4-[2-dimethylamino-1-(1-hydroxycyclohexyl)ethyl]phenyl 4-methylbenzoate hydrochloride, and a method for preparing the same. The compound of formula (I), as described in CN1955159A, is a white crystalline solid with a melting point of 203.2° C.-206.5° C.

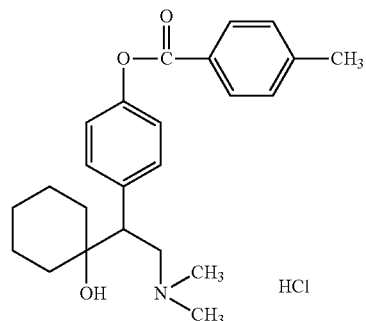

I

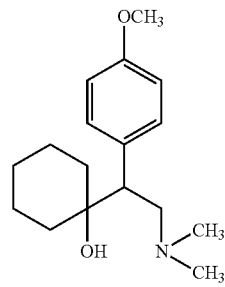

II

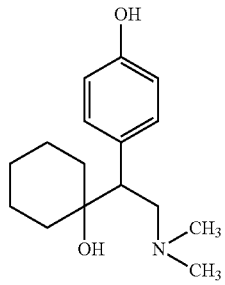

III

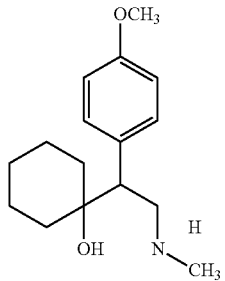

IV

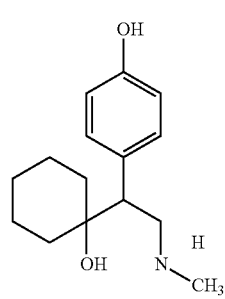

V

-continued

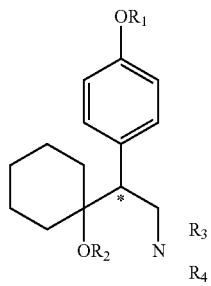

VI

BRIEF SUMMARY

Provided herein is a crystal form I of 4-[2-dimethylamino-1-(1-hydroxycyclohexyl)ethyl]phenyl 4-methylbenzoate hydrochloride, characterized in that the crystal form I exhibits a powder X-ray diffraction pattern obtained using CuKα radiation and having characteristic peaks expressed in degrees 2θ (±0.2° 2θ) at 10.690, 14.290, 16.030, 17.931, 19.009, 21.009 and 22.350.

The crystal form I exhibits a powder X-ray diffraction pattern having characteristic peaks expressed in degrees 2θ (±0.2° 2θ) at 10.690, 14.290, 15.328, 16.030, 17.931, 19.009, 21.009, 21.469, 22.350, 23.130, 24.969 and 25.232.

The crystal form I exhibits a powder X-ray diffraction pattern having characteristic peaks expressed in degrees 2θ (±0.2° 2θ) at 4.751, 8.329, 9.307, 10.690, 12.372, 14.290, 15.328, 16.030, 16.711, 17.432, 17.931, 18.433, 19.009, 19.750, 21.009, 21.469, 22.350, 23.130, 23.791, 24.149, 24.470, 24.969, 25.232, 26.491, 27.610, 28.449, 28.670, 29.511, 31.010, 31.572, 32.111, 32.789, 33.387, 34.590, 35.210, 36.070, 36.953, 38.027, 38.751 and 39.711.

The crystal form I exhibits a powder X-ray diffraction pattern substantially as shown in FIG. 1.

The crystal form I has a melting point of 213.0° C.-213.8° C.

The crystal form I has a DSC spectrum substantially as shown in FIG. 2.

Also provided herein is a crystal form II of 4-[2-dimethylamino-1-(1-hydroxycyclohexyl)ethyl]phenyl 4-methylbenzoate hydrochloride, characterized in that the crystal form II exhibits a powder X-ray diffraction pattern obtained using CuKα radiation and having characteristic peaks expressed in degrees 2θ (±0.2° 2θ) at 5.899, 11.799, 14.481, 15.440, 18.420, 19.800 and 23.620.

The crystal form II exhibits a powder X-ray diffraction pattern having characteristic peaks expressed in degrees 2θ (±0.2° 2θ) at 5.899, 11.799, 13.779, 14.481, 15.039, 15.440, 17.701, 18.420, 19.800, 23.620 and 25.220.

The crystal form II exhibits a powder X-ray diffraction pattern having characteristic peaks expressed in degrees 2θ (±0.2° 2θ) at 5.899, 10.280, 11.799, 13.779, 14.481, 15.039, 15.440, 15.920, 16.901, 17.701, 17.900, 18.420, 19.800, 20.679, 20.938, 21.819, 22.761, 23.242, 23.620, 24.799, 25.220, 26.001, 26.440, 26.717, 27.241, 27.780, 28.160, 28.719, 29.279, 29.796, 30.604, 31.340, 31.723, 31.901, 32.425, 32.939, 33.880, 34.282, 34.460, 35.141, 36.400, 37.225, 38.377 and 39.501.

The crystal form II exhibits a powder X-ray diffraction pattern substantially as shown in FIG. 3.

The crystal form II has a melting point of 209.5° C.-210.2° C.

The crystal form II has a DSC spectrum substantially as shown in FIG. 4.

Also provided herein is a crystal form III of 4-[2-dimethylamino-1-(1-hydroxycyclohexyl)ethyl]phenyl 4-methylbenzoate hydrochloride, wherein the melting point is 210.1-211.9° C.

A crystal form III of 4-[2-dimethylamino-1-(1-hydroxycyclohexyl)ethyl]phenyl 4-methylbenzoate hydrochloride has a DSC spectrum substantially as shown in FIG. 6.

Also provided herein is a crystal form IV of 4-[2-dimethylamino-1-(1-hydroxycyclohexyl)ethyl]phenyl 4-methylbenzoate hydrochloride, characterized in that the crystal form IV exhibits a powder X-ray diffraction pattern obtained using CuKα radiation and having characteristic peaks expressed in degrees 2θ (±0.2° 2θ) at 9.495, 11.135, 14.576, 15.954, 17.755, 19.114, 21.415, 23.475, 25.455 and 29.174.

The crystal form IV exhibits a powder X-ray diffraction pattern having characteristic peaks expressed in degrees 2θ (±0.2° 2θ) at 7.653, 9.136, 9.495, 11.135, 11.456, 11.714, 14.576, 15.954, 16.694, 16.995, 17.755, 18.234, 19.114, 20.176, 20.975, 21.415, 22.916, 23.475, 25.095, 25.455, 26.293 and 29.174.

The crystal form IV exhibits a powder X-ray diffraction pattern having characteristic peaks expressed in degrees 2θ (±0.2° 2θ) at 7.653, 9.136, 9.495, 11.135, 11.456, 11.714, 13.856, 14.576, 15.954, 16.694, 16.995, 17.755, 18.234, 19.114, 20.176, 20.975, 21.415, 22.037, 22.916, 23.475, 25.095, 25.455, 26.015, 26.293, 27.075, 28.035, 28.735, 29.174, 30.356, 31.916, 32.449, 33.473, 33.774, 34.714, 35.675, 36.195, 36.952, 38.596, 39.197 and 39.794.

The crystal form IV exhibits a powder X-ray diffraction pattern substantially as shown in FIG. 7.

The crystal form IV has a melting point of 213.2° C.-213.9° C.

The crystal form IV has a DSC spectrum substantially as shown in FIG. 8.

Also provided herein is a crystal form V of 4-[2-dimethylamino-1-(1-hydroxycyclohexyl)ethyl]phenyl 4-methylbenzoate hydrochloride, characterized in that the crystal form V exhibits a powder X-ray diffraction pattern obtained using CuKα radiation and having characteristic peaks expressed in degrees 2θ (±0.2° 2θ) at 6.540, 13.541, 16.321, 17.200, 18.860, 19.520 and 19.940.

The crystal form V exhibits a powder X-ray diffraction pattern having characteristic peaks expressed in degrees 2θ (±0.2° 2θ) at 3.801, 6.540, 9.941, 11.280, 13.039, 13.541, 16.321, 17.200, 18.860, 19.520, 19.940 and 24.660.

The crystal form V exhibits a powder X-ray diffraction pattern having characteristic peaks expressed in degrees 2θ (±0.2° 2θ) at 3.801, 6.540, 9.941, 11.280, 13.039, 13.541, 15.039, 15.534, 16.321, 17.200, 18.860, 19.520, 19.940, 22.901, 23.580, 24.660, 25.841, 26.320, 27.521, 28.598, 29.538, 30.880, 31.365, 32.421, 33.800 and 34.539.

The crystal form V exhibits a powder X-ray diffraction pattern substantially as shown in FIG. 9.

The crystal form V has a melting point of 211.8° C.-212.8° C.

The crystal form V has a DSC spectrum substantially as shown in FIG. 10.

Also provided herein is a method for preparing the crystal form I, comprising: dissolving 4-[2-dimethylamino-1-(1-hydroxycyclohexyl)ethyl]phenyl 4-methylbenzoate hydrochloride in a solvent; and recrystallizing at 10° C.-70° C. under normal pressure or vacuum (−0.1 Mpa), wherein the solvent is any one or a mixture of any two solvents of methanol, ethanol, n-propanol, isopropanol or n-butanol, chloroform, carbon tetrachloride or dichloroethane, DMF, dioxane, pyridine, ethyl acetate, acetonitrile, and petroleum ether, the volume ratio of the two solvents in the mixture is 1:10 to 10:1, and the ratio of the weight of 4-[2-dimethylamino-1-(1-hydroxycyclohexyl)ethyl]phenyl 4-methylbenzoate hydrochloride (mg) to the volume of the solvent (ml) is 100:1 to 4:1.

A method for preparing the crystal form I, comprising: dissolving 4-[2-dimethylamino-1-(1-hydroxycyclohexyl)ethyl]phenyl 4-methylbenzoate hydrochloride in dichloromethane or acetonitrile; and recrystallizing at 40° C.-60° C. under normal pressure.

A method for preparing the crystal form I, comprising maintaining 4-[2-dimethylamino-1-(1-hydroxycyclohexyl)ethyl]phenyl 4-methylbenzoate hydrochloride at 100° C.-150° C. in the absence of a solvent for 1-6 h.

The crystal form I is obtained by 4-[2-dimethylamino-1-(1-hydroxycyclohexyl)ethyl]phenyl 4-methylbenzoate hydrochloride according to conditions in Table 7.

Also provided herein is a method for preparing the crystal form II, comprising: dissolving 4-[2-dimethylamino-1-(1-hydroxycyclohexyl)ethyl]phenyl 4-methylbenzoate hydrochloride in water and recrystallizing at 25° C.-40° C.

A method for preparing the crystal form II, comprising dissolving 4-[2-dimethylamino-1-(1-hydroxycyclohexyl)ethyl]phenyl 4-methylbenzoate hydrochloride in acetonitrile and recrystallizing at 25° C., wherein the ratio of the weight of 4-[2-dimethylamino-1-(1-hydroxycyclohexyl)ethyl]phenyl 4-methylbenzoate hydrochloride (mg) to the volume of the solvent (ml) is 10:1 to 20:1.

A method for preparing the crystal form II, comprising placing 4-[2-dimethylamino-1-(1-hydroxycyclohexyl)ethyl]phenyl 4-methylbenzoate hydrochloride at 25° C. under a humidity of 75%-92.5% in the absence of a solvent for 5-10 days.

The crystal form II is obtained by 4-[2-dimethylamino-1-(1-hydroxycyclohexyl)ethyl]phenyl 4-methylbenzoate hydrochloride according to conditions in Table 8.

Also provided herein is a method for preparing the crystal form III, comprising: dissolving 4-[2-dimethylamino-1-(1-hydroxycyclohexyl)ethyl]phenyl 4-methylbenzoate hydrochloride in dichloromethane or chloroform; and recrystallizing 4-[2-dimethylamino-1-(1-hydroxycyclohexyl)ethyl]phenyl 4-methylbenzoate hydrochloride at 50° C. under vacuum (−0.09 Mpa), wherein the ratio of the weight of 4-[2-dimethylamino-1-(1-hydroxycyclohexyl)ethyl]phenyl 4-methylbenzoate hydrochloride (mg) to the volume of the solvent (ml) is 20:1 to 25:1.

A method for preparing the crystal form III, comprising heating 4-[2-dimethylamino-1-(1-hydroxycyclohexyl)ethyl]phenyl 4-methylbenzoate hydrochloride at a temperature of 115° C. in the absence of a solvent for a period of time, e.g., 8 minutes.

A method for preparing the crystal form III, characterized in that 4-[2-dimethylamino-1-(1-hydroxycyclohexyl)ethyl]phenyl 4-methylbenzoate hydrochloride is subjected to physical destruction of the molecular lattice.

Also provided herein is a method for preparing the crystal form IV, comprising dissolving 4-[2-dimethylamino-1-(1-hydroxycyclohexyl)ethyl]phenyl 4-methylbenzoate hydrochloride in a mixed solvent of dimethyl sulfoxide and ethyl acetate; and recrystallizing 4-[2-dimethylamino-1-(1-hydroxycyclohexyl)ethyl]phenyl 4-methylbenzoate hydrochloride at 18° C., wherein the ratio of the weight of 4-[2-dimethylamino-1-(1-hydroxycyclohexyl)ethyl]phenyl 4-methylbenzoate hydrochloride (mg) to the volume of the solvent (ml) is 10:1 to 15:1, and the volume ratio of dimethyl sulfoxide to ethyl acetate is 1:10.

Also provided herein is a method for preparing the crystal form V, comprising: dissolving 4-[2-dimethylamino-1-(1-hydroxycyclohexyl)ethyl]phenyl 4-methylbenzoate hydrochloride in a mixed solvent of chloroform and petroleum ether or a mixed solvent of dichloromethane and petroleum ether; and recrystallizing 4-[2-dimethylamino-1-(1-hydroxycyclohexyl)ethyl]phenyl 4-methylbenzoate hydrochloride at 18° C., wherein the ratio of the weight of 4-[2-dimethylamino-1-(1-hydroxycyclohexyl)ethyl]phenyl 4-methylbenzoate hydrochloride (mg) to the volume of the solvent (ml) is 9:1 to 20:1, and the volume ratio of chloroform to petroleum ether or the volume ratio of dichloromethane to petroleum ether is 1:10.

Further provided is use of any one or combination of the crystal form I, the crystal form II, the crystal form III, the crystal form IV and the crystal form V in the preparation of a medicament for treating diseases associated with 5-hydroxytryptamine (5-HT) and/or norepinephrine (NA) reuptake, preferably, the diseases associated with 5-hydroxytryptamine (5-HT) and/or norepinephrine (NA) reuptake are central nervous system diseases, more preferably, depression, anxiety disorder, panic disorder, agoraphobia, post traumatic stress disorder, premenstrual dysphoric disorder, fibromyalgia, attention deficit disorder, obsessive-compulsive syndrome, autistic disorder, autism, schizophrenia, obesity, hyperorexia nervosa and anorexia nervosa, Tourette syndrome, vasomotor flushing, cocaine or alcohol addiction, sexual disturbance, borderline personality disorder, chronic fatigue syndrome, urinary incontinence, pain, Shy Drager syndrome, Raynaud syndrome, Parkinson's disease, or epilepsy.

DETAILED DESCRIPTION

Figure 1:
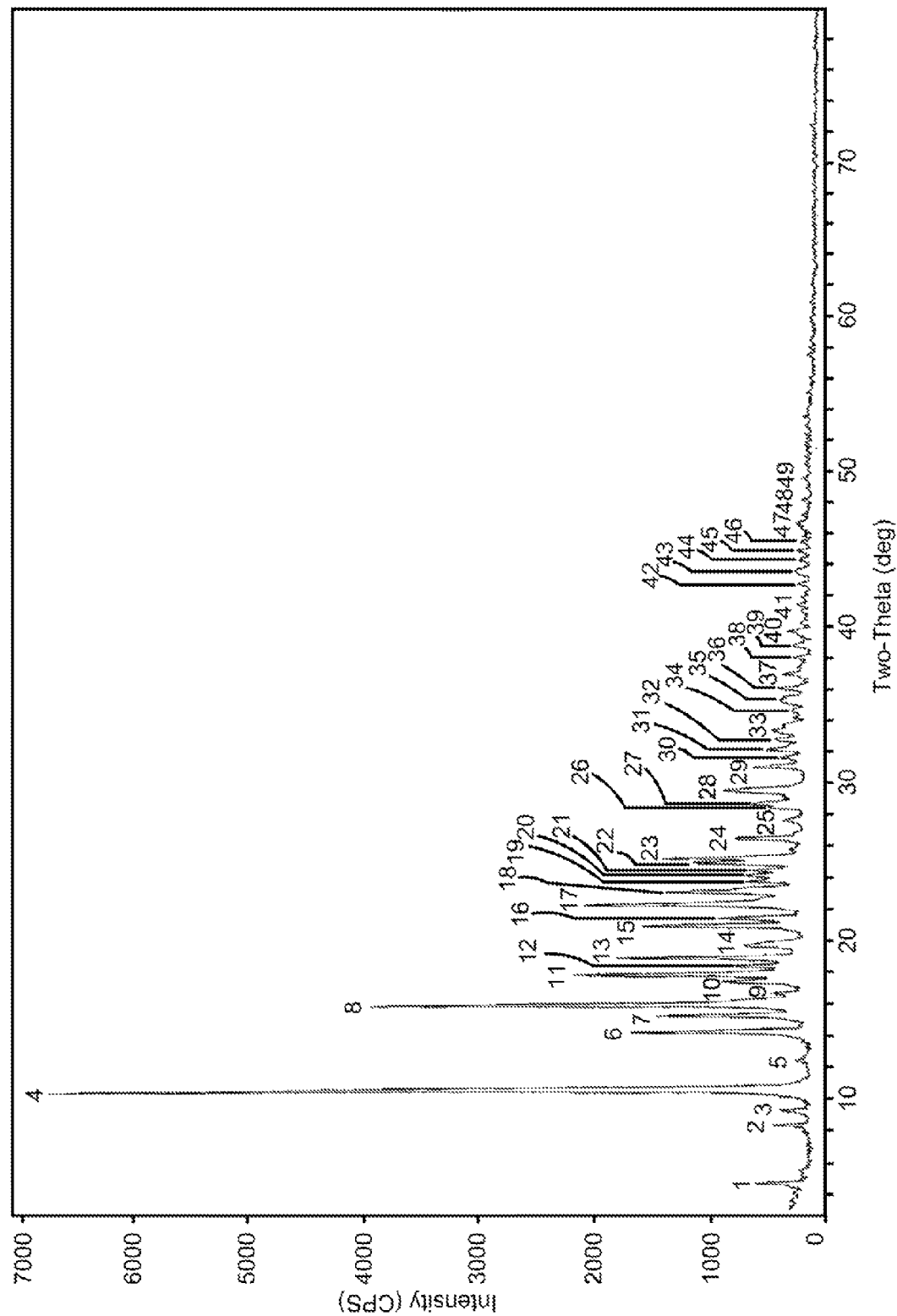
FIG. 1 is a powder X-ray diffractogram of a crystal form I.

Crystal forms of a drug describe the existence states of the drug molecules. Solid drugs generally have heteromorphism, and the drugs with different crystal forms have different crystal structures and consequently may have different physical and chemical properties such as melting points, solubility and stability, thereby influencing production, storage and transport, stability and safety of the drug. The purpose of research on the crystal form is to increase efficacy and safety of the drug. The stability of the crystal form may influence the stability of the drug, thereby influencing efficacy, dosage and safety of the drug. Chinese Patent No. CN1955159A has disclosed the compound 4-[2-dimethylamino-1-(1-hydroxycyclohexyl)ethyl]phenyl 4-methylbenzoate hydrochloride.

It has been found by the inventors that the stability and bioavailability of certain crystal forms of the compound 4-[2-dimethylamino-1-(1-hydroxycyclohexyl)ethyl]phenyl 4-methylbenzoate hydrochloride and its various solvates are better than the compound 4-[2-dimethylamino-1-(1-hydroxycyclohexyl)ethyl]phenyl 4-methylbenzoate hydrochloride of CN1955159A (m.p. 203.2° C.-206.5° C.).

One embodiment provides polymorphs of a compound of formula (I), [4-[2-dimethylamino-1-(1-hydroxycyclohexyl)ethyl]phenyl 4-methylbenzoate hydrochloride], comprising a crystal form I, a crystal form II, a crystal form III, a crystal form IV and a crystal form V

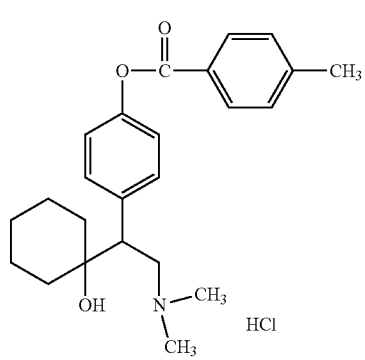

(I)

Another embodiment of the present disclosure provides methods for preparing a crystal form I, a crystal form II, a crystal form III, a crystal form IV and a crystal form V of a compound of formula (I).

A further embodiment of the present disclosure provides a pharmaceutical composition, comprising an effective amount of any one or combination of a crystal form I, a crystal form II, a crystal form III, a crystal form IV and a crystal form V of a compound of formula (I), and a pharmaceutically acceptable carrier.

Yet another embodiment of the present disclosure provides use of any one of a crystal form I, a crystal form II, a crystal form III, a crystal form IV and a crystal form V of a compound of formula (I) in the preparation of a medicament for treating diseases associated with 5-hydroxytryptamine (5-HT) and/or norepinephrine (NA) reuptake.

In one preferred embodiment of the present disclosure, the diseases associated with 5-hydroxytryptamine (5-HT) and/or norepinephrine (NA) reuptake are central nervous system diseases, preferably, depression, anxiety disorder, panic disorder, agoraphobia, post traumatic stress disorder, premenstrual dysphoric disorder, fibromyalgia, attention deficit disorder, obsessive-compulsive syndrome, autistic disorder, autism, schizophrenia, obesity, hyperorexia nervosa and anorexia nervosa, Tourette syndrome, vasomotor flushing, cocaine or alcohol addiction, sexual disturbance, borderline personality disorder, chronic fatigue syndrome, urinary incontinence, pain, Shy Drager syndrome, Raynaud syndrome, Parkinson's disease, or epilepsy.

In one embodiment, a crystal form I of a compound of formula (I) exhibits a powder X-ray diffraction pattern obtained using CuK$_\alpha$ radiation and having characteristic peaks expressed in degrees 2θ (±0.2° 2θ) at 10.690, 14.290, 16.030, 17.931, 19.009, 21.009 and 22.350; preferably, exhibits a powder X-ray diffraction pattern having characteristic peaks expressed in degrees 2θ (±0.2° 2θ) at 10.690, 14.290, 15.328, 16.030, 17.931, 19.009, 21.009, 21.469, 22.350, 23.130, 24.969 and 25.232; more preferably, exhibits a powder X-ray diffraction pattern having characteristic peaks expressed in degrees 2θ (±0.2° 2θ) at 4.751, 8.329, 9.307, 10.690, 12.372, 14.290, 15.328, 16.030, 16.711, 17.432, 17.931, 18.433, 19.009, 19.750, 21.009, 21.469, 22.350, 23.130, 23.791, 24.149, 24.470, 24.969, 25.232, 26.491, 27.610, 28.449, 28.670, 29.511, 31.010, 31.572, 32.111, 32.789, 33.387, 34.590, 35.210, 36.070, 36.953, 38.027, 38.751 and 39.711; most preferably, exhibits a powder X-ray diffraction pattern substantially as shown in FIG. 1.

Figure 2:
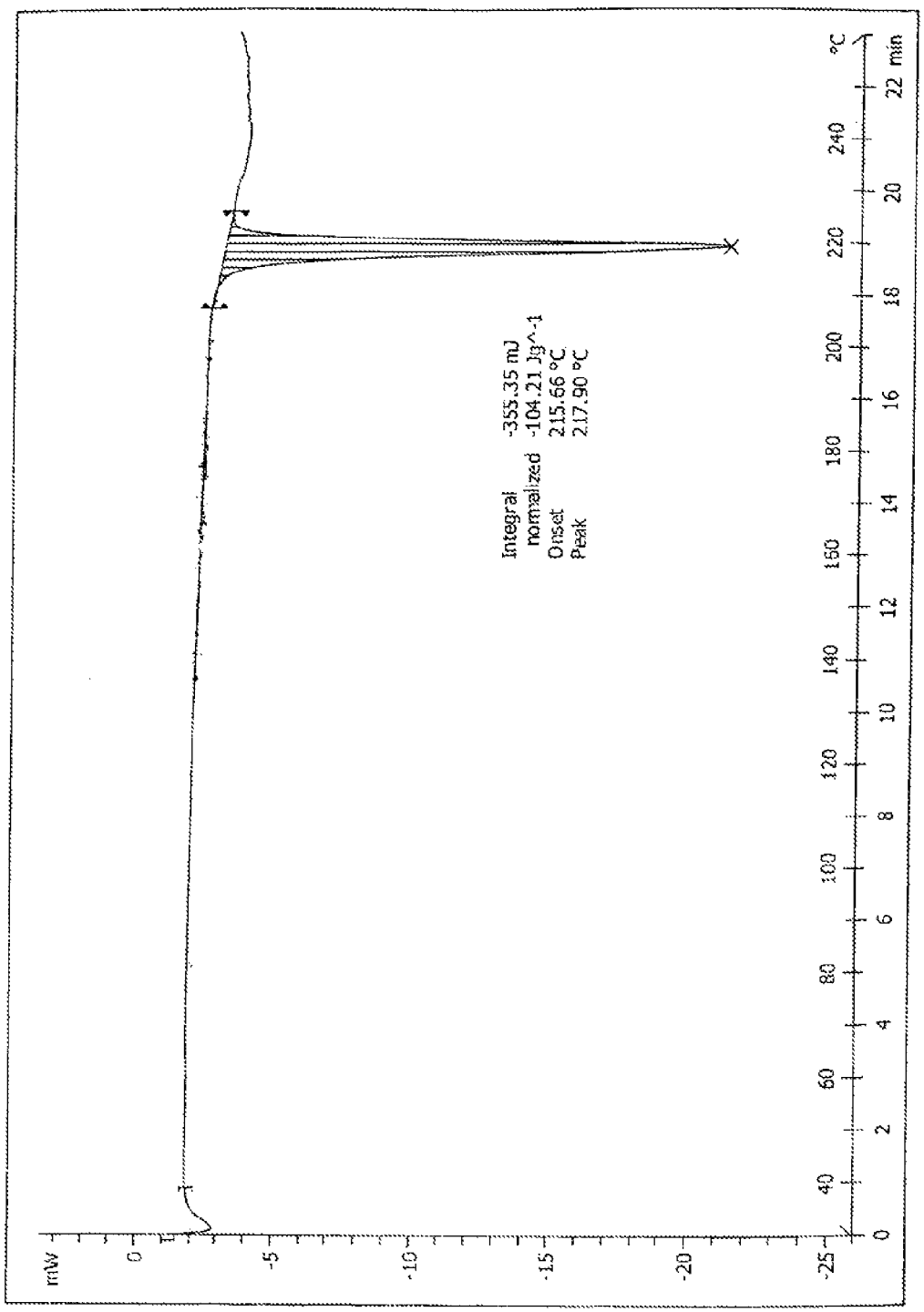
FIG. 2 is a DSC spectrum of a crystal form I.

In one preferred embodiment of the present disclosure, the crystal form I has a melting point of 213.0° C.-213.8° C. and a DSC (differential scanning calorimetry) spectrum substantially as shown in FIG. 2, which has an endothermic peak at 218° C.

Figure 11:
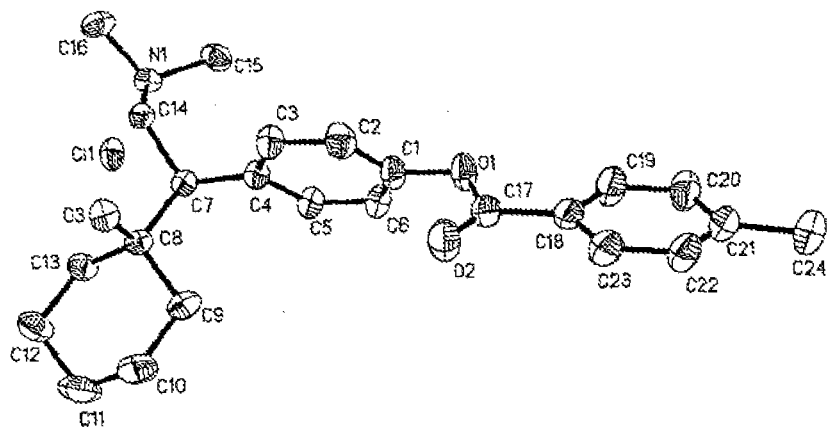
FIG. 11 is a projection graph of a single crystal diffraction molecular three-dimensional structure of a crystal form I.
Figure 12:
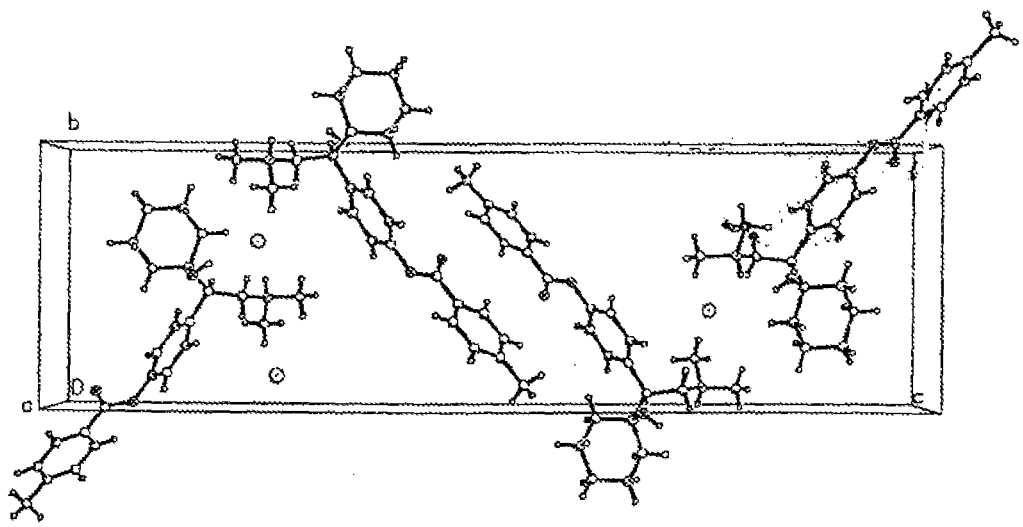
FIG. 12 is a single crystal diffraction molecular unit cell stacking graph of a crystal form I.
Figure 13:
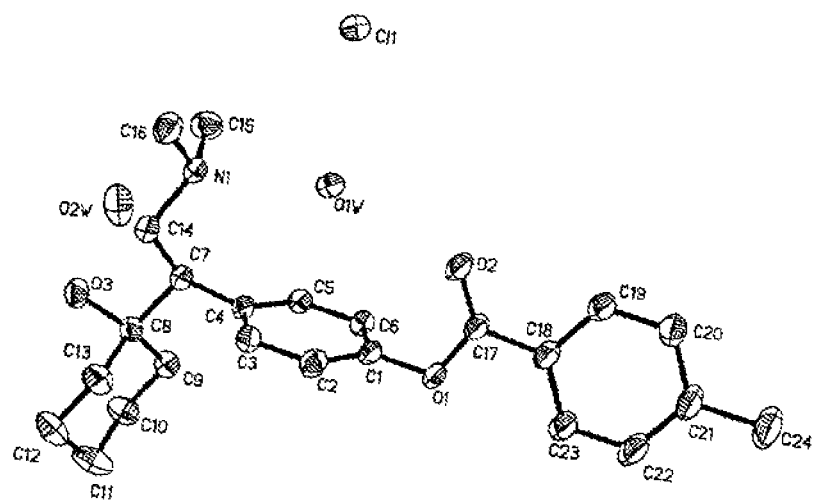
FIG. 13 is a projection graph of a single crystal diffraction molecular three-dimensional structure of a crystal form II.

In one preferred embodiment of the present disclosure, the crystal form I has single crystal diffraction bond length shown in Table 1 and single crystal diffraction bond angle shown in Table 2. The size of the crystal used in the diffraction test is 0.12×0.18×0.50 mm. The crystal belongs to the monoclinic system and the space group P2$_1$/c with unit cell parameters: a=5.775(2) Å, b=11.072(3) Å, c=37.361(1) Å, and β=90.007(5)°. The unit cell volume is V=2388.9(11) Å$^3$, and the number of molecules in the unit cell is Z=4. The stoichiometric formula in an asymmetrical unit is determined as C$_{24}$H$_{31}$NO$_3$.HCl, and the density of the crystal is 1.162 g/cm$^3$. The projection graph of a single crystal diffraction molecular three-dimensional structure of a crystal form I is shown in FIG. 11; The single crystal diffraction molecular unit cell stacking graph of a crystal form I is shown in FIG. 12;

TABLE 1

| Single Crystal Diffraction Bond Length of Crystal Form I | | | |
|---|---|---|---|
| N(1)—C(15) | 1.482(2) | C(7)—C(8) | 1.566(2) |
| N(1)—C(14) | 1.487(2) | C(7)—H(7A) | 0.9800 |
| N(1)—C(16) | 1.491(2) | C(8)—C(9) | 1.530(2) |
| N(1)—H(10C) | 0.9100 | C(8)—C(13) | 1.532(2) |
| O(1)—C(17) | 1.354(2) | C(9)—C(10) | 1.521(3) |

TABLE 1-continued

Single Crystal Diffraction Bond Length of Crystal Form I

| Atoms | Length | Atoms | Length |
|---|---|---|---|
| O(1)—C(1) | 1.407(2) | C(9)—H(9A) | 0.9700 |
| O(2)—C(17) | 1.195(2) | C(9)—H(9B) | 0.9700 |
| O(3)—C(8) | 1.434(2) | C(10)—C(11) | 1.529(3) |
| O(3)—H(3B) | 0.81(2) | C(10)—H(10A) | 0.9700 |
| C(1)—C(2) | 1.370(3) | C(10)—H(10B) | 0.9700 |
| C(1)—C(6) | 1.371(2) | C(11)—C(12) | 1.512(3) |
| C(2)—C(3) | 1.392(2) | C(11)—H(11A) | 0.9700 |
| C(2)—H(2A) | 0.9300 | C(11)—H(11B) | 0.9700 |
| C(3)—C(4) | 1.389(2) | C(12)—C(13) | 1.524(3) |
| C(3)—H(3A) | 0.9300 | C(12)—H(12A) | 0.9700 |
| C(4)—C(5) | 1.387(2) | C(12)—H(12B) | 0.9700 |
| C(4)—C(7) | 1.520(2) | C(13)—H(13A) | 0.9700 |
| C(5)—C(6) | 1.392(2) | C(13)—H(13B) | 0.9700 |
| C(5)—H(5A) | 0.9300 | C(14)—H(14A) | 0.9700 |
| C(6)—H(6A) | 0.9300 | C(14)—H(14B) | 0.9700 |
| C(7)—C(14) | 1.536(2) | C(15)—H(15A) | 0.9600 |
| C(15)—H(15B) | 0.9600 | C(15)—H(15C) | 0.9600 |
| C(16)—H(16A) | 0.9600 | C(16)—H(16B) | 0.9600 |
| C(16)—H(16C) | 0.9600 | C(17)—C(18) | 1.482(2) |
| C(18)—C(19) | 1.376(3) | C(18)—C(23) | 1.376(3) |
| C(19)—C(20) | 1.386(3) | C(19)—H(19A) | 0.9300 |
| C(20)—C(21) | 1.369(4) | C(20)—H(20A) | 0.9300 |
| C(21)—C(22) | 1.364(4) | C(21)—C(24) | 1.517(3) |
| C(22)—C(23) | 1.381(3) | C(22)—H(22A) | 0.9300 |
| C(23)—H(23A) | 0.9300 | C(24)—H(24A) | 0.9600 |
| C(24)—H(24B) | 0.9600 | C(24)—H(24C) | 0.9600 |

TABLE 2

Single Crystal Diffraction Bond Angle of Crystal Form I

| Atoms | Angle | Atoms | Angle |
|---|---|---|---|
| C(15)—N(1)—C(14) | 113.6(1) | C(9)—C(8)—C(13) | 109.1(1) |
| C(15)—N(1)—C(16) | 111.1(1) | O(3)—C(8)—C(7) | 109.1(1) |
| C(14)—N(1)—C(16) | 110.3(1) | C(9)—C(8)—C(7) | 112.2(1) |
| C(15)—N(1)—H(10C) | 107.2 | C(13)—C(8)—C(7) | 109.7(1) |
| C(14)—N(1)—H(10C) | 107.2 | C(10)—C(9)—C(8) | 112.3(2) |
| C(16)—N(1)—H(10C) | 107.2 | C(10)—C(9)—H(9A) | 109.2 |
| C(17)—O(1)—C(1) | 118.1(1) | C(8)—C(9)—H(9A) | 109.2 |
| C(8)—O(3)—H(3B) | 103.6(2) | C(10)—C(9)—H(9B) | 109.2 |
| C(2)—C(1)—C(6) | 121.5(1) | C(8)—C(9)—H(9B) | 109.2 |
| C(2)—C(1)—O(1) | 122.0(2) | H(9A)—C(9)—H(9B) | 107.9 |
| C(6)—C(1)—O(1) | 116.4(2) | C(9)—C(10)—C(11) | 111.8(2) |
| C(1)—C(2)—C(3) | 119.2(2) | C(9)—C(10)—H(10A) | 109.3 |
| C(1)—C(2)—H(2A) | 120.4 | C(11)—C(10)—H(10A) | 109.3 |
| C(3)—C(2)—H(2A) | 120.4 | C(9)—C(10)—H(10B) | 109.3 |
| C(4)—C(3)—C(2) | 120.8(2) | C(11)—C(10)—H(10B) | 109.3 |
| C(4)—C(3)—H(3A) | 119.6 | H(10A)—C(10)—H(10B) | 107.9 |
| C(2)—C(3)—H(3A) | 119.6 | C(12)—C(11)—C(10) | 110.4(2) |
| C(5)—C(4)—C(3) | 118.3(1) | C(12)—C(11)—H(11A) | 109.6 |
| C(5)—C(4)—C(7) | 119.4(1) | C(10)—C(11)—H(11A) | 109.6 |
| C(3)—C(4)—C(7) | 122.2(1) | C(12)—C(11)—H(11B) | 109.6 |
| C(4)—C(5)—C(6) | 121.2(2) | C(10)—C(11)—H(11B) | 109.6 |
| C(4)—C(5)—H(5A) | 119.4 | H(11A)—C(11)—H(11B) | 108.1 |
| C(6)—C(5)—H(5A) | 119.4 | C(11)—C(12)—C(13) | 110.3(2) |
| C(1)—C(6)—C(5) | 118.9(2) | C(11)—C(12)—H(12A) | 109.6 |
| C(1)—C(6)—H(6A) | 120.5 | C(13)—C(12)—H(12A) | 109.6 |
| C(5)—C(6)—H(6A) | 120.5 | C(11)—C(12)—H(12B) | 109.6 |
| C(4)—C(7)—C(14) | 113.4(1) | C(13)—C(12)—H(12B) | 109.6 |
| C(4)—C(7)—C(8) | 113.4(1) | H(12A)—C(12)—H(12B) | 108.1 |
| C(14)—C(7)—C(8) | 108.8(1) | C(12)—C(13)—C(8) | 112.5(1) |
| C(4)—C(7)—H(7A) | 107.0 | C(12)—C(13)—H(13A) | 109.1 |
| C(14)—C(7)—H(7A) | 107.0 | C(8)—C(13)—H(13A) | 109.1 |
| C(8)—C(7)—H(7A) | 107.0 | C(12)—C(13)—H(13B) | 109.1 |
| O(3)—C(8)—C(9) | 106.2(1) | C(8)—C(13)—H(13B) | 109.1 |
| O(3)—C(8)—C(13) | 110.5(1) | H(13A)—C(13)—H(13B) | 107.8 |
| N(1)—C(14)—C(7) | 114.1(1) | C(23)—C(18)—C(17) | 118.7(2) |
| N(1)—C(14)—H(14A) | 108.7 | C(18)—C(19)—C(20) | 119.7(2) |
| C(7)—C(14)—H(14A) | 108.7 | C(18)—C(19)—H(19A) | 120.2 |
| N(1)—C(14)—H(14B) | 108.7 | C(20)—C(19)—H(19A) | 120.2 |
| C(7)—C(14)—H(14B) | 108.7 | C(21)—C(20)—C(19) | 121.7(2) |
| H(14A)—C(14)—H(14B) | 107.6 | C(21)—C(20)—H(20A) | 119.1 |
| N(1)—C(15)—H(15A) | 109.5 | C(19)—C(20)—H(20A) | 119.1 |
| N(1)—C(15)—H(15B) | 109.5 | C(22)—C(21)—C(20) | 117.7(2) |
| H(15A)—C(15)—H(15B) | 109.5 | C(22)—C(21)—C(24) | 121.6(3) |
| N(1)—C(15)—H(15C) | 109.5 | C(20)—C(21)—C(24) | 120.7(3) |
| H(15A)—C(15)—H(15C) | 109.5 | C(21)—C(22)—C(23) | 121.9(2) |
| H(15B)—C(15)—H(15C) | 109.5 | C(21)—C(22)—H(22A) | 119.1 |
| N(1)—C(16)—H(16A) | 109.5 | C(23)—C(22)—H(22A) | 119.1 |
| N(1)—C(16)—H(16B) | 109.5 | C(18)—C(23)—C(22) | 119.9(2) |
| H(16A)—C(16)—H(16B) | 109.5 | C(18)—C(23)—H(23A) | 120.0 |
| N(1)—C(16)—H(16C) | 109.5 | C(22)—C(23)—H(23A) | 120.0 |
| H(16A)—C(16)—H(16C) | 109.5 | C(21)—C(24)—H(24A) | 109.5 |
| H(16B)—C(16)—H(16C) | 109.5 | C(21)—C(24)—H(24B) | 109.5 |
| O(2)—C(17)—O(1) | 123.1(2) | H(24A)—C(24)—H(24B) | 109.5 |
| O(2)—C(17)—C(18) | 125.6(2) | C(21)—C(24)—H(24C) | 109.5 |
| O(1)—C(17)—C(18) | 111.3(2) | H(24A)—C(24)—H(24C) | 109.5 |

TABLE 2-continued

| Single Crystal Diffraction Bond Angle of Crystal Form I | | | |
|---|---|---|---|
| C(19)—C(18)—C(23) | 119.0(2) | H(24B)—C(24)—H(24C) | 109.5 |
| C(19)—C(18)—C(17) | 122.3(2) | | |

Figure 3:
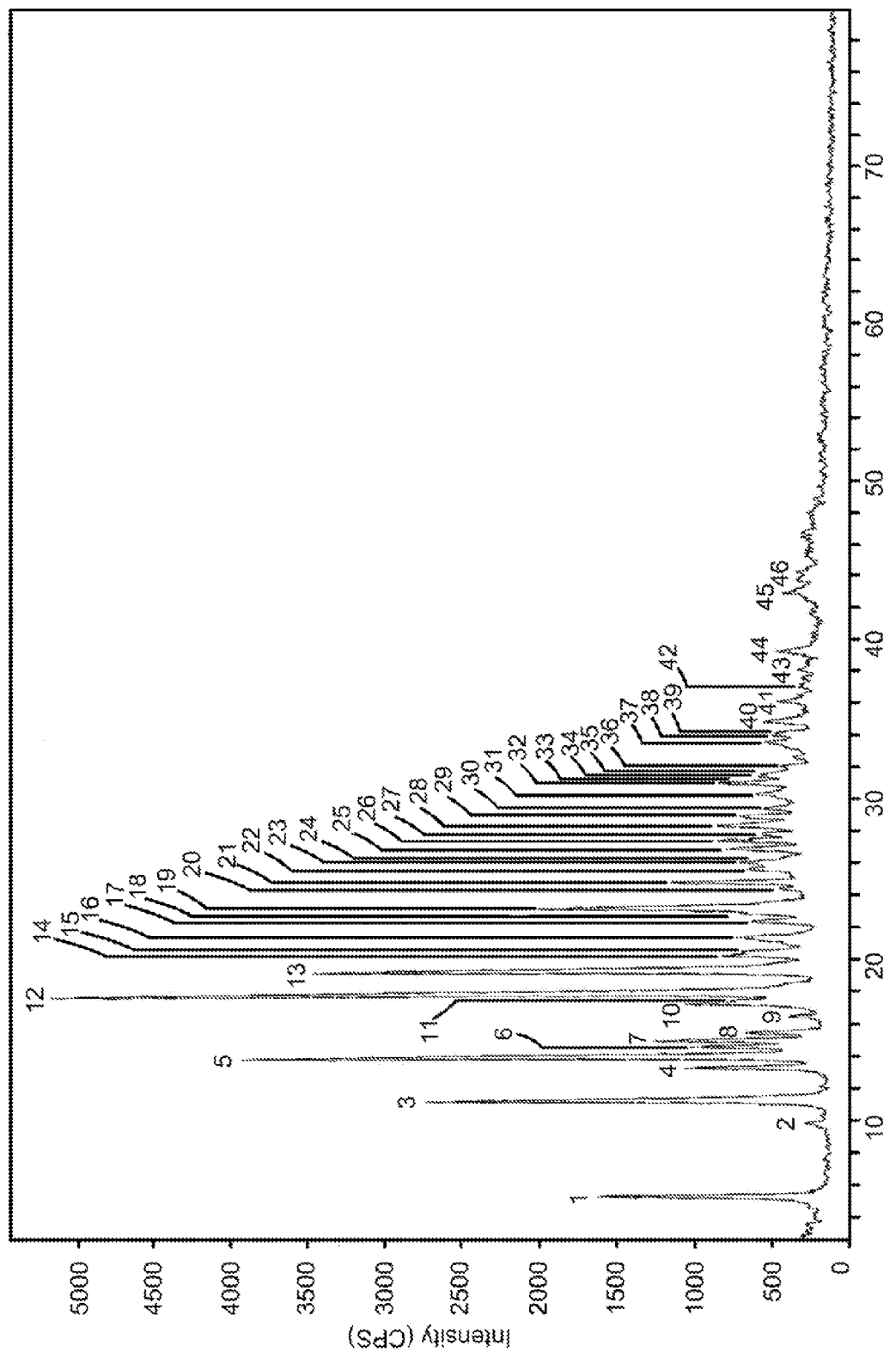
FIG. 3 is a powder X-ray diffractogram of a crystal form II.

Another embodiment provides a crystal form II of a compound of formula (I), which is a hydrate (i.e., 4-[2-dimethylamino-1-(1-hydroxycyclohexyl)ethyl]phenyl 4-methylbenzoate hydrochloride hydrate) of the compound of formula (I). The crystal form II exhibits a powder X-ray diffraction pattern obtained using $CuK_\alpha$ radiation and having characteristic peaks expressed in degrees 2θ (±0.2° 2θ) at 5.899, 11.799, 14.481, 15.440, 18.420, 19.800 and 23.620; preferably, exhibits a powder X-ray diffraction pattern having characteristic peaks expressed in degrees 2θ (±0.2° 2θ) at 5.899, 11.799, 13.779, 14.481, 15.039, 15.440, 17.701, 18.420, 19.800, 23.620 and 25.220; more preferably, exhibits a powder X-ray diffraction pattern having characteristic peaks expressed in degrees 2θ (±0.2° 2θ) at 5.899, 10.280, 11.799, 13.779, 14.481, 15.039, 15.440, 15.920, 16.901, 17.701, 17.900, 18.420, 19.800, 20.679, 20.938, 21.819, 22.761, 23.242, 23.620, 24.799, 25.220, 26.001, 26.440, 26.717, 27.241, 27.780, 28.160, 28.719, 29.279, 29.796, 30.604, 31.340, 31.723, 31.901, 32.425, 32.939, 33.880, 34.282, 34.460, 35.141, 36.400, 37.225, 38.377 and 39.501; most preferably, exhibits a powder X-ray diffraction pattern substantially as shown in FIG. 3.

Figure 4:
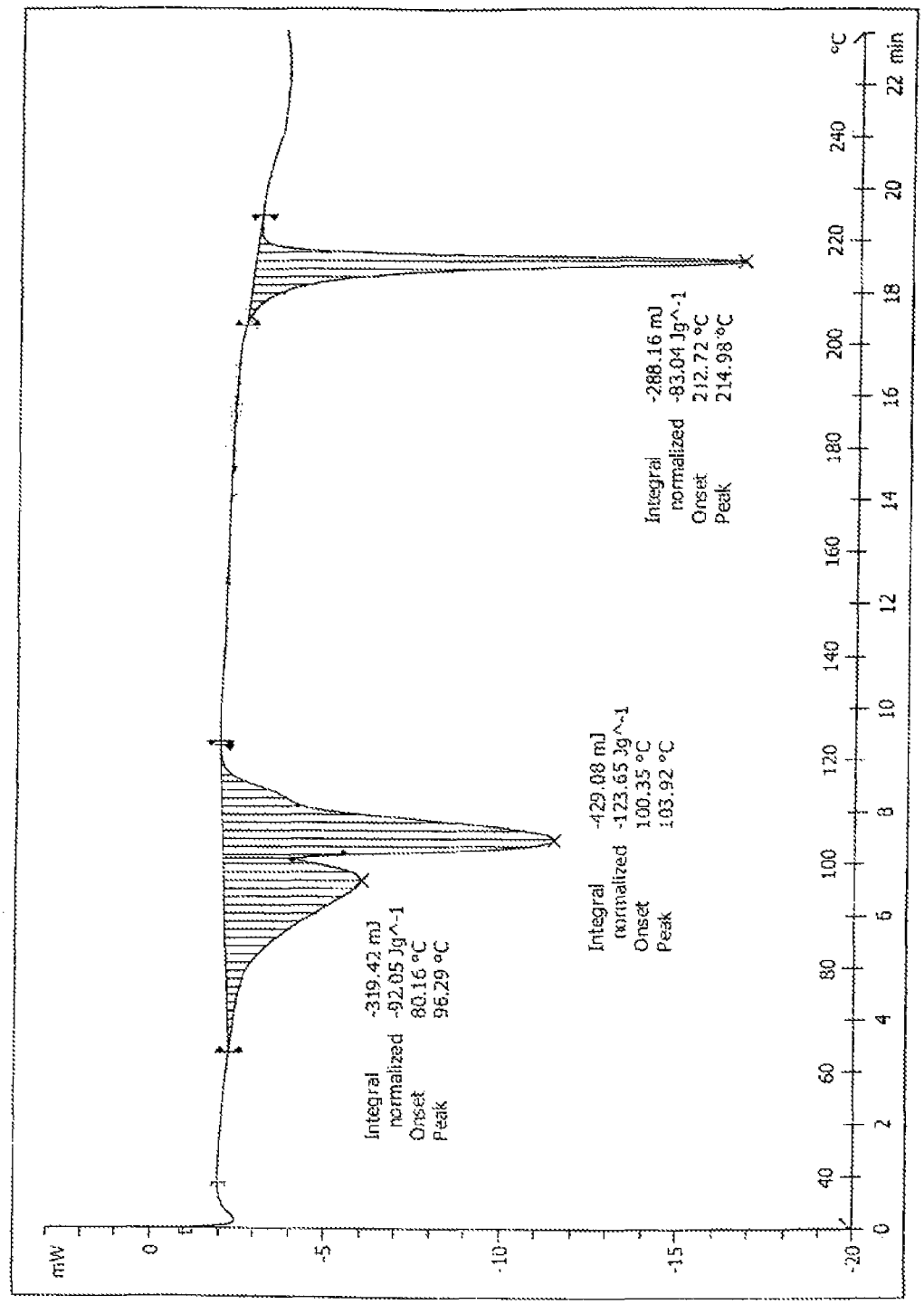
FIG. 4 is a DSC spectrum of a crystal form II.

In one preferred embodiment of the present disclosure, the crystal form II has a melting point of 209.5° C.-210.2° C. and a DSC spectrum substantially as shown in FIG. 4, which has three endothermic peaks at 96° C., 104° C. and 215° C. respectively.

Figure 14:
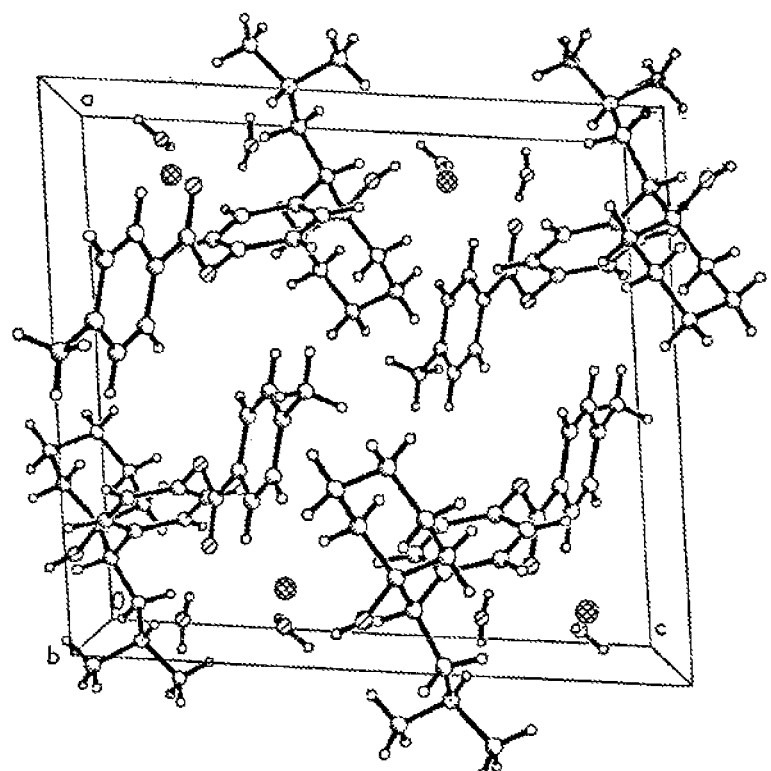
FIG. 14 is a single crystal diffraction molecular unit cell stacking graph of a crystal form II.

In one preferred embodiment of the present disclosure, the crystal form II has single crystal diffraction bond length shown in Table 3 and single crystal diffraction bond angle shown in Table 4. The size of the crystal used in the diffraction test is 0.44×0.45×1.00 mm. The crystal belongs to the monoclinic system and the space group $P2_1/c$ with unit cell parameters: a=15.081(6) Å, b=10.459 (5) Å, c=16.380 (7) Å, and β=96.34(1)°. The unit cell volume is V=2567.7(1) Å$^3$, and the number of molecules in the unit cell is Z=4. The stoichiometric formula in an asymmetrical unit is determined as $C_{24}H_{31}NO_3 \cdot HCl \cdot (H_2O)_2$, and the density of the crystal is 1.174 g/cm$^3$. The single crystal diffraction molecular unit cell stacking graph of a crystal form II is shown in FIG. 14.

TABLE 3

| Single Crystal Diffraction Bond Length of Crystal Form II | | | |
|---|---|---|---|
| N(1)—C(15) | 1.475(3) | C(3)—H(3B) | 0.9300 |
| N(1)—C(16) | 1.499(3) | C(4)—C(5) | 1.390(3) |
| N(1)—C(14) | 1.508(3) | C(4)—C(7) | 1.526(2) |
| N(1)—H(1N) | 0.95(5) | C(5)—C(6) | 1.381(3) |
| O(1)—C(17) | 1.351(2) | C(5)—H(5A) | 0.9300 |
| O(1)—C(1) | 1.414(2) | C(6)—H(6A) | 0.9300 |
| O(2)—C(17) | 1.205(2) | C(7)—C(14) | 1.526(3) |
| O(3)—C(8) | 1.433(2) | C(7)—C(8) | 1.565(3) |
| O(3)—H(3A) | 0.8200 | C(7)—H(7A) | 0.9800 |
| C(1)—C(6) | 1.369(3) | C(8)—C(13) | 1.524(3) |
| C(1)—C(2) | 1.372(3) | C(8)—C(9) | 1.525(3) |
| C(2)—C(3) | 1.392(3) | C(9)—C(10) | 1.529(3) |
| C(2)—H(2A) | 0.9300 | C(9)—H(9A) | 0.9700 |
| C(3)—C(4) | 1.387(3) | C(9)—H(9B) | 0.9700 |
| C(10)—C(11) | 1.514(4) | C(17)—C(18) | 1.474(2) |
| C(10)—H(10A) | 0.9700 | C(18)—C(23) | 1.387(3) |
| C(10)—H(10B) | 0.9700 | C(18)—C(19) | 1.387(3) |
| C(11)—C(12) | 1.513(5) | C(19)—C(20) | 1.371(3) |
| C(11)—H(11A) | 0.9700 | C(19)—H(19A) | 0.9300 |
| C(11)—H(11B) | 0.9700 | C(20)—C(21) | 1.387(3) |
| C(12)—C(13) | 1.533(3) | C(20)—C(20A) | 0.9300 |
| C(12)—H(12A) | 0.9700 | C(21)—C(22) | 1.390(4) |
| C(12)—H(12B) | 0.9700 | C(21)—C(24) | 1.517(3) |
| C(13)—H(13A) | 0.9700 | C(22)—C(23) | 1.375(3) |
| C(13)—H(13B) | 0.9700 | C(22)—H(22A) | 0.9300 |
| C(14)—H(14A) | 0.9700 | C(23)—H(23A) | 0.9300 |
| C(14)—H(14B) | 0.9700 | C(24)—H(24A) | 0.9600 |
| C(15)—H(15A) | 0.9600 | C(24)—H(24B) | 0.9600 |
| C(15)—H(15B) | 0.9600 | C(24)—H(24C) | 0.9600 |
| C(15)—H(15C) | 0.9600 | O(1W)—H(1WA) | 0.8500 |
| C(16)—H(16A) | 0.9600 | O(1W)—H(1WB) | 0.8500 |
| C(16)—H(16B) | 0.9600 | O(2W)—H(2WA) | 0.8499 |
| C(16)—H(16C) | 0.9600 | O(2W)—C(2WB) | 0.8500 |

TABLE 4

| Single Crystal Diffraction Bond Angle of Crystal Form II | | | |
|---|---|---|---|
| C(15)—N(1)—C(16) | 109.4(2) | C(5)—C(6)—H(6A) | 120.3 |
| C(15)—N(1)—C(14) | 114.5(2) | C(4)—C(7)—C(14) | 110.4(2) |
| C(16)—N(1)—C(14) | 109.7(2) | C(4)—C(7)—C(8) | 115.1(2) |
| C(15)—N(1)—H(1N) | 106(3) | C(14)—C(7)—C(8) | 112.3(2) |
| C(16)—N(1)—H(1N) | 105(3) | C(4)—C(7)—H(7A) | 106.1 |
| C(14)—N(1)—H(1N) | 112(3) | C(14)—C(7)—H(7A) | 106.1 |
| C(17)—O(1)—C(1) | 116.1(1) | C(8)—C(7)—H(7A) | 106.1 |
| C(8)—O(3)—H(3A) | 109.5 | O(3)—C(8)—C(13) | 105.6(2) |
| C(6)—C(1)—C(2) | 121.5(2) | O(3)—C(8)—C(9) | 110.1(2) |
| C(6)—C(1)—O(1) | 119.3(2) | C(13)—C(8)—C(9) | 110.2(2) |
| C(2)—C(1)—O(1) | 119.1(2) | O(3)—C(8)—C(7) | 107.3(2) |
| C(1)—C(2)—C(3) | 118.8(2) | C(13)—C(8)—C(7) | 115.4(2) |
| C(1)—C(2)—H(2A) | 120.6 | C(9)—C(8)—C(7) | 108.1(2) |
| C(3)—C(2)—H(2A) | 120.6 | C(8)—C(9)—C(10) | 112.2(2) |
| C(4)—C(3)—C(2) | 121.1(2) | C(8)—C(9)—H(9A) | 109.2 |
| C(4)—C(3)—H(3B) | 119.5 | C(10)—C(9)—H(9A) | 109.2 |
| C(2)—C(3)—H(3B) | 119.5 | C(8)—C(9)—H(9B) | 109.2 |
| C(5)—C(4)—C(3) | 118.3(2) | C(10)—C(9)—H(9B) | 109.2 |
| C(5)—C(4)—C(7) | 118.3(2) | H(9A)—C(9)—H(9B) | 107.9 |
| C(3)—C(4)—C(7) | 123.2(2) | C(11)—C(10)—C(9) | 110.6(2) |

TABLE 4-continued

Single Crystal Diffraction Bond Angle of Crystal Form II

| | | | |
|---|---|---|---|
| C(6)—C(5)—C(4) | 121.0(2) | C(11)—C(10)—H(10A) | 109.5 |
| C(6)—C(5)—H(5A) | 119.5 | C(9)—C(10)—H(10A) | 109.5 |
| C(4)—C(5)—H(5A) | 119.5 | C(11)—C(10)—H(10B) | 109.5 |
| C(1)—C(6)—C(5) | 119.4(2) | C(9)—C(10)—H(10B) | 109.5 |
| C(1)—C(6)—H(6A) | 120.3 | H(10A)—C(10)—H(10B) | 108.1 |
| C(10)—C(11)—C(12) | 110.8(2) | N(1)—C(16)—H(16C) | 109.5 |
| C(10)—C(11)—H(11A) | 109.5 | H(16A)—C(16)—H(16C) | 109.5 |
| C(12)—C(11)—H(11A) | 109.5 | H(16B)—C(16)—H(16C) | 109.5 |
| C(12)—C(11)—H(11B) | 109.5 | O(2)—C(17)—O(1) | 122.1(2) |
| C(10)—C(11)—H(11B) | 109.5 | O(2)—C(17)—C(18) | 125.2(2) |
| H(11A)—C(11)—H(11B) | 108.1 | O(1)—C(17)—C(18) | 112.7(2) |
| C(11)—C(12)—C(13) | 111.5(2) | C(23)—C(18)—C(19) | 119.1(2) |
| C(11)—C(12)—H(12A) | 109.3 | C(23)—C(18)—C(17) | 122.6(2) |
| C(13)—C(12)—H(12A) | 109.3 | C(19)—C(18)—C(17) | 118.3(2) |
| C(11)—C(12)—H(12B) | 109.3 | C(20)—C(19)—C(18) | 120.7(2) |
| C(13)—C(12)—H(12B) | 109.3 | C(20)—C(19)—H(19A) | 119.7 |
| H(12A)—C(12)—H(12B) | 108.0 | C(18)—C(19)—H(19A) | 119.7 |
| C(8)—C(13)—C(12) | 111.3(2) | C(19)—C(20)—C(21) | 121.0(2) |
| C(8)—C(13)—H(13A) | 109.4 | C(19)—C(20)—H(20A) | 119.5 |
| C(12)—C(13)—H(13A) | 109.4 | C(21)—C(20)—H(20A) | 119.5 |
| C(8)—C(13)—H(13B) | 109.4 | C(20)—C(21)—C(22) | 117.9(2) |
| C(12)—C(13)—H(13B) | 109.4 | C(20)—C(21)—C(24) | 120.3(2) |
| H(13A)—C(13)—H(13B) | 108.0 | C(22)—C(21)—C(24) | 121.8(2) |
| N(1)—C(14)—C(7) | 110.8(2) | C(23)—C(22)—C(21) | 121.6(2) |
| N(1)—C(14)—H(14A) | 109.5 | C(23)—C(22)—H(22A) | 119.2 |
| C(7)—C(14)—H(14A) | 109.5 | C(21)—C(22)—H(22A) | 119.2 |
| N(1)—C(14)—H(14B) | 109.5 | C(22)—C(23)—C(18) | 119.8(2) |
| C(7)—C(14)—H(14B) | 109.5 | C(22)—C(23)—H(23A) | 120.1 |
| H(14A)—C(14)—H(14B) | 108.1 | C(18)—C(23)—H(23A) | 120.1 |
| N(1)—C(15)—H(15A) | 109.5 | C(21)—C(24)—H(24A) | 109.5 |
| N(1)—C(15)—H(15B) | 109.5 | C(21)—C(24)—H(24B) | 109.5 |
| H(15A)—C(15)—H(15B) | 109.5 | H(24A)—C(24)—H(24B) | 109.5 |
| N(1)—C(15)—H(15C) | 109.5 | C(21)—C(24)—H(24C) | 109.5 |
| H(15A)—C(15)—H(15C) | 109.5 | H(24A)—C(24)—H(24C) | 109.5 |
| H(15B)—C(15)—H(15C) | 109.5 | H(24B)—C(24)—H(24C) | 109.5 |
| N(1)—C(16)—H(16A) | 109.5 | H(1WA)—O(1W)—H(1WB) | 104.9 |
| N(1)—C(16)—H(16B) | 109.5 | H(2WA)—O(2W)—H(2WB) | 102.3 |
| H(16A)—C(16)—H(16B) | 109.5 | | |

Figure 5:
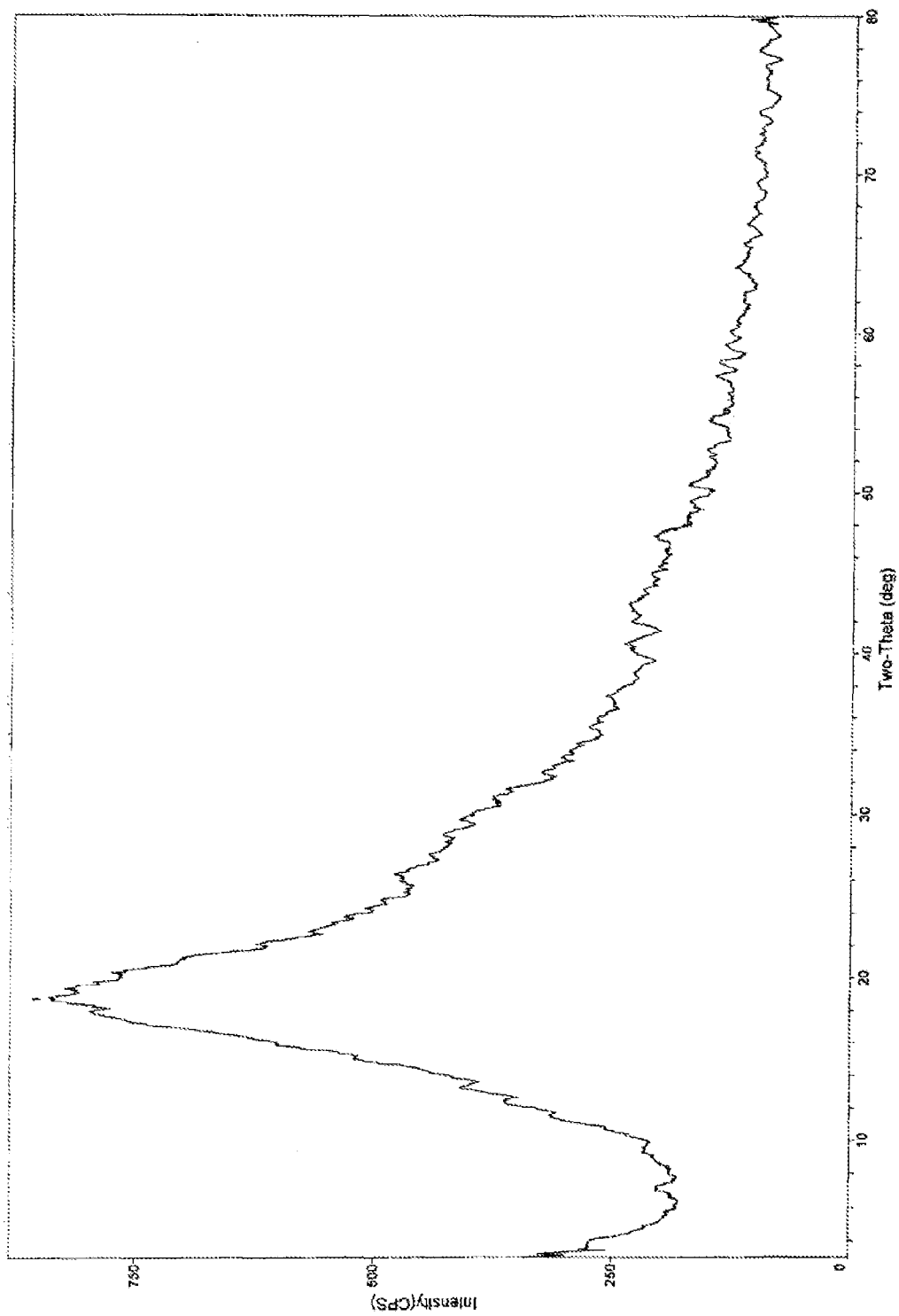
FIG. 5 is a powder X-ray diffractogram of a crystal form III.

Another embodiment of the present disclosure provides a crystal form III of a compound of formula (I). The crystal form III exhibits a powder X-ray diffraction pattern obtained using CuK$_\alpha$ radiation and having a characteristic peak expressed in degrees 2θ (±0.2° 2θ) at 18.840; preferably, exhibits a powder X-ray diffraction pattern substantially as shown in FIG. 5.

Figure 6:
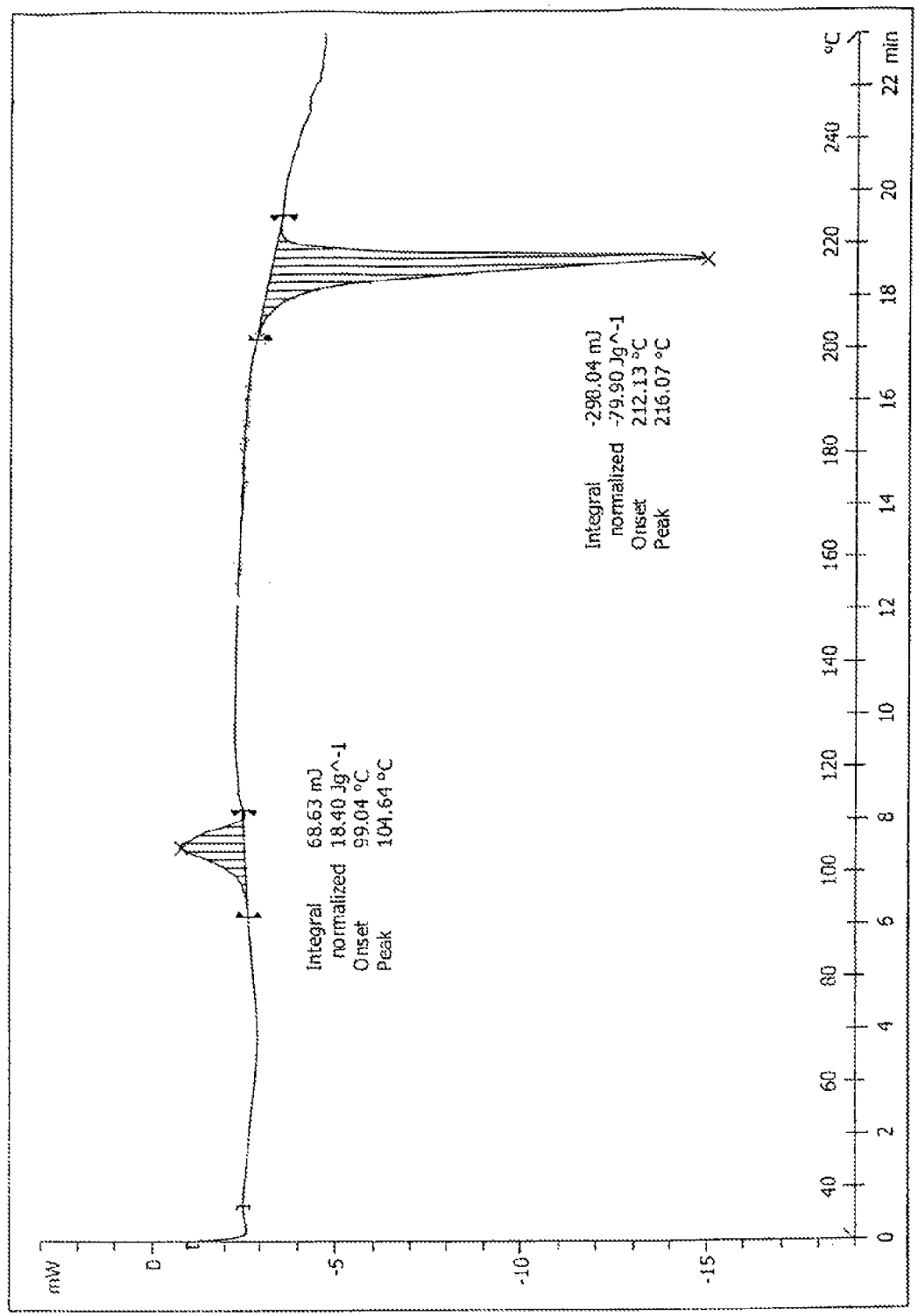
FIG. 6 is a DSC spectrum of a crystal form III.

In one preferred embodiment of the present disclosure, the crystal form III has a melting point of 210.1-211.9° C. and a DSC (differential scanning calorimetry) spectrum substantially as shown in FIG. 6, which has an endothermic peak at 216° C. and an exothermic peak at 105° C.

Figure 7:
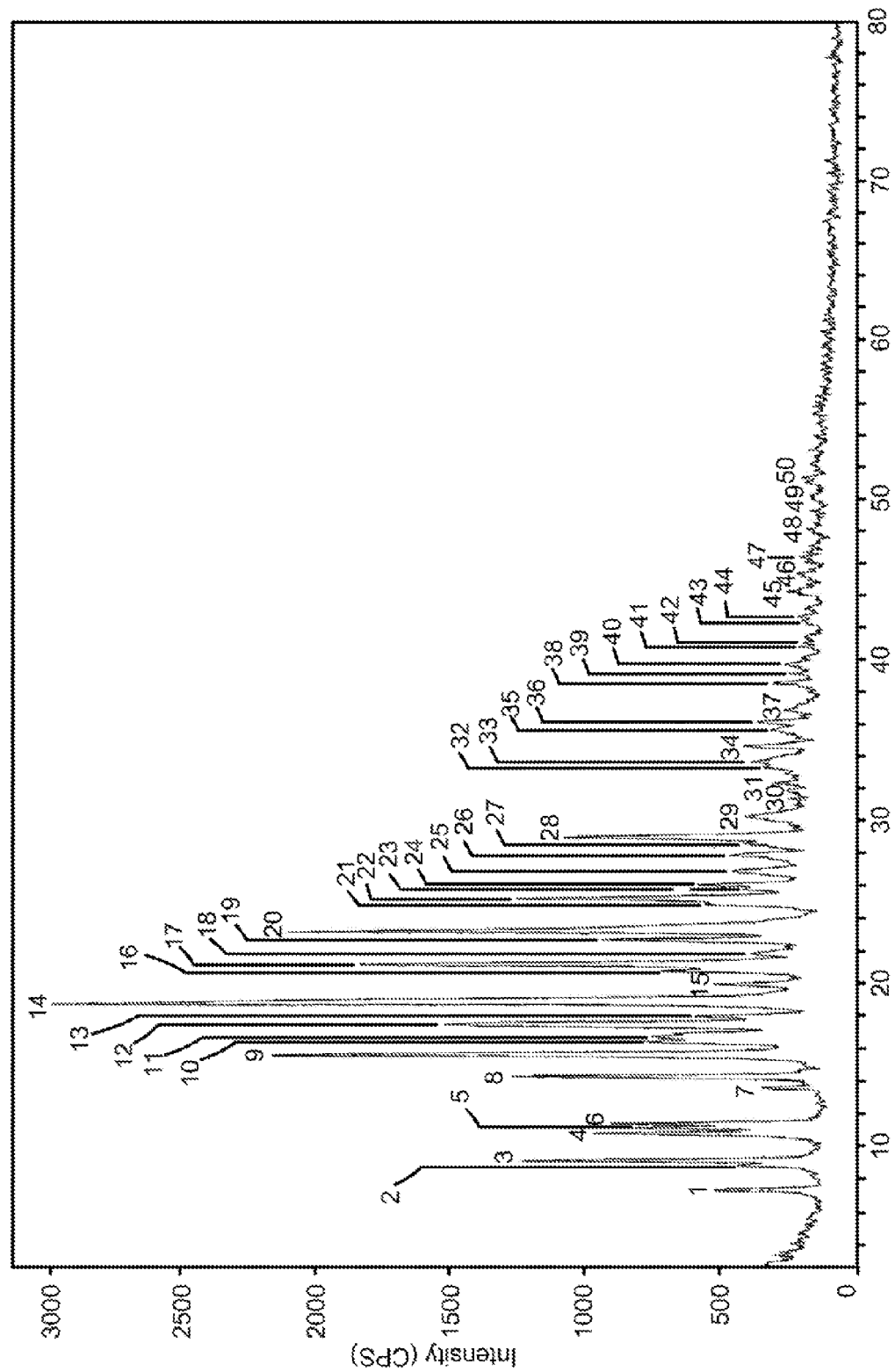
FIG. 7 is a powder X-ray diffractogram of a crystal form IV.

Another embodiment provides a crystal form IV of a compound of formula (I), which is a dimethyl sulfoxide solvate of (i.e., 4-[2-dimethylamino-1-(1-hydroxycyclohexyl)ethyl]phenyl 4-methylbenzoate hydrochloride dimethyl sulfoxide solvate) of the compound of formula (I). The crystal form IV exhibits a powder X-ray diffraction pattern obtained using CuK$_\alpha$ radiation and having characteristic peaks expressed in degrees 2θ (±0.2° 2θ) at 9.495, 11.135, 14.576, 15.954, 17.755, 19.114, 21.415, 23.475, 25.455 and 29.174; preferably, exhibits a powder X-ray diffraction pattern having characteristic peaks expressed in degrees 2θ (±0.2° 2θ) at 7.653, 9.136, 9.495, 11.135, 11.456, 11.714, 14.576, 15.954, 16.694, 16.995, 17.755, 18.234, 19.114, 20.176, 20.975, 21.415, 22.916, 23.475, 25.095, 25.455, 26.293 and 29.174; more preferably, exhibits a powder X-ray diffraction pattern having characteristic peaks expressed in degrees 2θ (±0.2° 2θ) at 7.653, 9.136, 9.495, 11.135, 11.456, 11.714, 13.856, 14.576, 15.954, 16.694, 16.995, 17.755, 18.234, 19.114, 20.176, 20.975, 21.415, 22.037, 22.916, 23.475, 25.095, 25.455, 26.015, 26.293, 27.075, 28.035, 28.735, 29.174, 30.356, 31.916, 32.449, 33.473, 33.774, 34.714, 35.675, 36.195, 36.952, 38.596, 39.197 and 39.794; further preferably, exhibits a powder X-ray diffraction pattern substantially as shown in FIG. 7.

Figure 8:
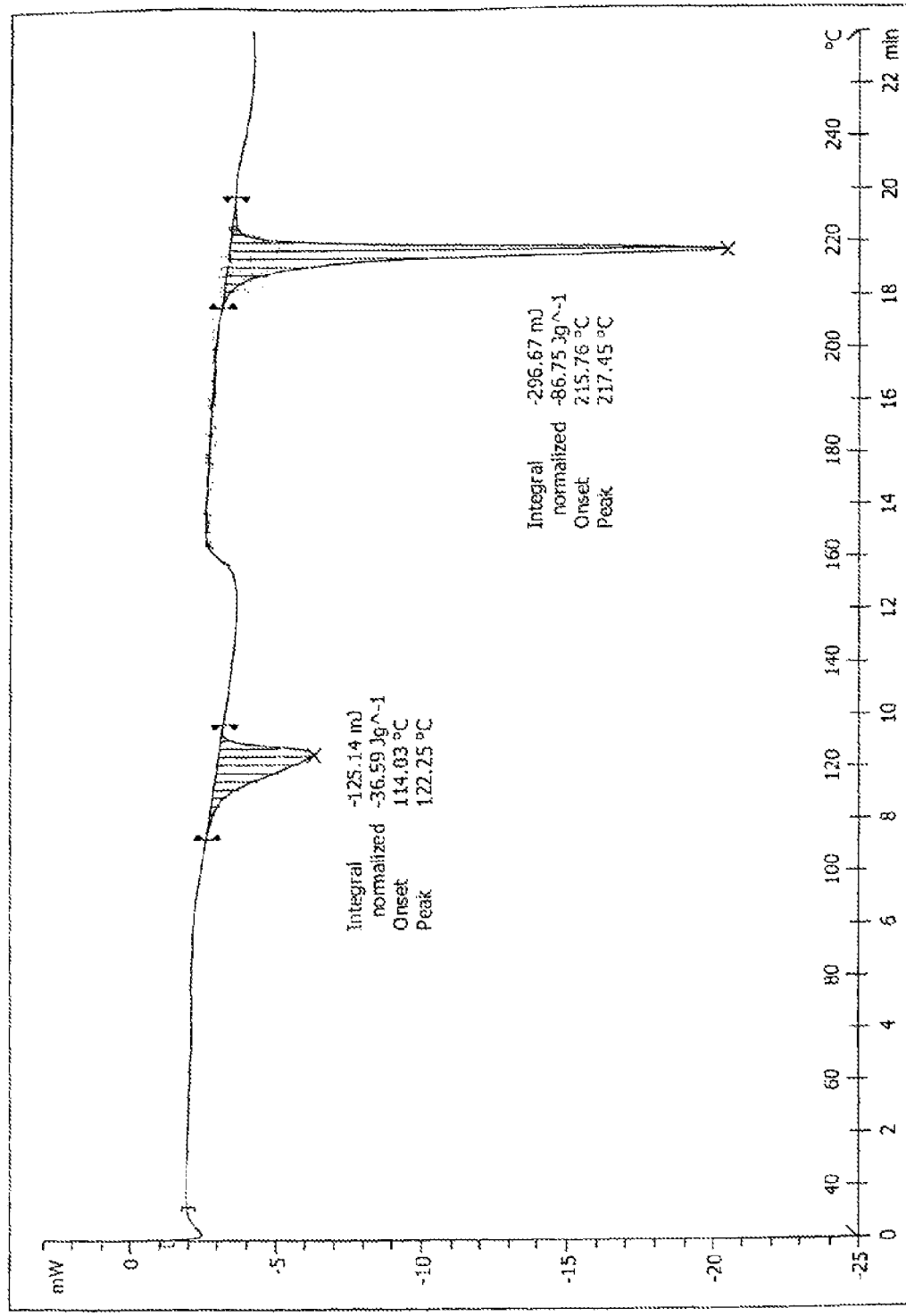
FIG. 8 is a DSC spectrum of a crystal form IV.

In one preferred embodiment of the present disclosure, the crystal form IV has a melting point of 213.2° C.-213.9° C. and a DSC spectrum substantially as shown in FIG. 8, which has two endothermic peaks at 122° C. and 217° C. respectively.

Figure 15:
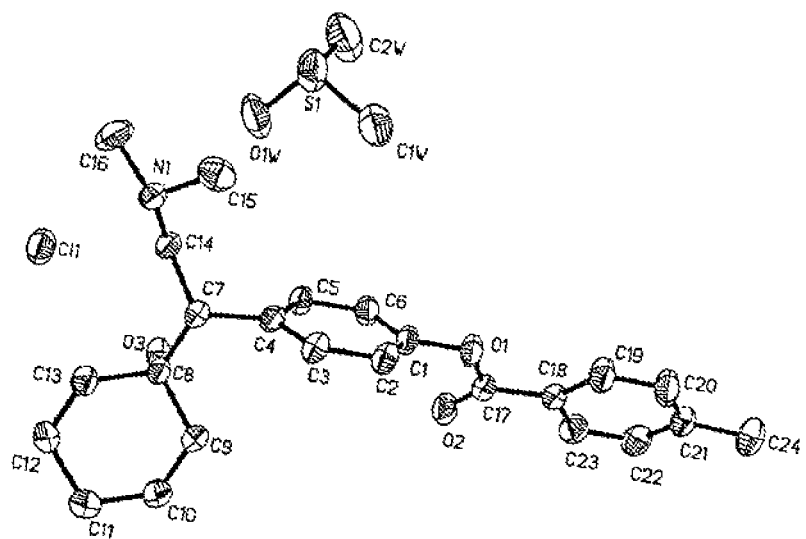
FIG. 15 is a projection graph of a single crystal diffraction molecular three-dimensional structure of a crystal form IV.
Figure 16:
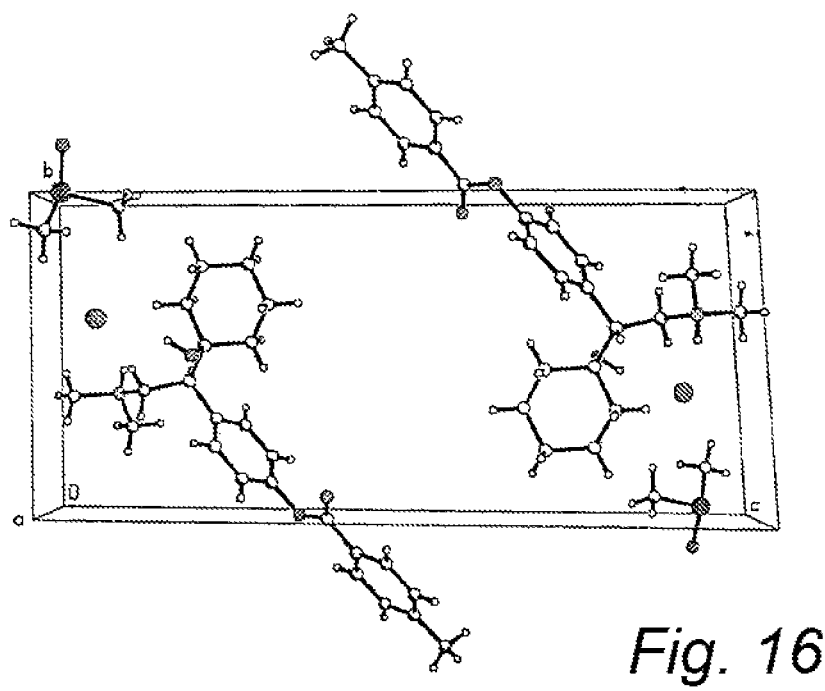
FIG. 16 is a single crystal diffraction molecular unit cell stacking graph of a crystal form IV.

In one preferred embodiment of the present disclosure, the crystal form IV has single crystal diffraction bond length shown in Table 5 and single crystal diffraction bond angle shown in Table 6. The size of the crystal used in the diffraction test is 0.12×0.18×0.24 mm. The crystal belongs to the triclinic system and the space group P-1 with unit cell parameters: a=5.704(1) Å, b=10.617(2) Å, c=23.446(4) Å, α=86.23(1)°, β=84.33(2)°, and γ=81.16(1)°. The unit cell volume is V=1394.2(4) Å$^3$, and the number of molecules in the unit cell is Z=2. The stoichiometric formula in an asymmetrical unit is determined as $C_{24}H_{31}NO_3 \cdot HCl \cdot C_2H_6SO$, and the density of the crystal is 1.183 g/cm$^3$. The projection graph of a single crystal diffraction molecular three-dimensional structure of a crystal form IV is shown in FIG. 15; The single crystal diffraction molecular unit cell stacking graph of a crystal form IV is shown in FIG. 16;

TABLE 5

Single Crystal Diffraction Bond Length of Crystal Form IV

| Bond | Length | Bond | Length |
|---|---|---|---|
| N(1)—C(15) | 1.481(3) | C(2)—C(3) | 1.388(3) |
| N(1)—C(14) | 1.483(2) | C(2)—H(2A) | 0.9300 |
| N(1)—C(16) | 1.490(3) | C(3)—C(4) | 1.394(2) |
| N(1)—H(1N) | 0.9100 | C(3)—H(3B) | 0.9300 |
| O(1)—C(17) | 1.357(2) | C(4)—C(5) | 1.384(3) |
| O(1)—C(1) | 1.407(2) | C(4)—C(7) | 1.520(2) |
| O(2)—C(17) | 1.197(2) | C(5)—C(6) | 1.386(2) |
| O(3)—C(8) | 1.438(2) | C(5)—H(5A) | 0.9300 |
| O(3)—H(3A) | 0.89(2) | C(6)—H(6A) | 0.9300 |
| C(1)—C(2) | 1.370(3) | C(7)—C(14) | 1.533(2) |
| C(1)—C(6) | 1.378(3) | C(7)—C(8) | 1.564(2) |
| C(7)—H(7A) | 0.9800 | C(17)—C(18) | 1.480(2) |
| C(8)—C(9) | 1.525(2) | C(18)—C(19) | 1.374(3) |
| C(9)—C(10) | 1.519(3) | C(18)—C(23) | 1.378(3) |
| C(8)—C(13) | 1.531(2) | C(19)—C(20) | 1.383(3) |
| C(9)—H(9A) | 0.9700 | C(19)—H(19A) | 0.9300 |
| C(9)—H(9B) | 0.9700 | C(20)—C(21) | 1.375(4) |
| C(10)—C(11) | 1.522(3) | C(20)—H(20A) | 0.9300 |
| C(10)—H(10A) | 0.9700 | C(21)—C(22) | 1.367(4) |
| C(10)—H(10B) | 0.9700 | C(21)—C(24) | 1.509(3) |
| C(11)—C(12) | 1.520(3) | C(22)—C(23) | 1.384(3) |
| C(11)—H(11A) | 0.9700 | C(22)—H(22A) | 0.9300 |
| C(11)—H(11B) | 0.9700 | C(23)—H(23A) | 0.9300 |
| C(12)—C(13) | 1.519(3) | C(24)—H(24A) | 0.9600 |
| C(12)—H(12A) | 0.9700 | C(24)—H(24B) | 0.9600 |
| C(12)—H(12B) | 0.9700 | C(24)—H(24C) | 0.9600 |
| C(13)—H(13A) | 0.9700 | S(1)—O(1W) | 1.539(3) |
| C(13)—H(13B) | 0.9700 | S(1)—C(2W) | 1.648(5) |
| C(14)—H(14A) | 0.9700 | S(1)—C(1W) | 1.768(4) |
| C(14)—H(14B) | 0.9700 | C(1W)—H(1WB) | 0.9600 |
| C(15)—H(15A) | 0.9600 | C(1W)—H(1WC) | 0.9600 |
| C(15)—H(15B) | 0.9600 | C(1W)—H(1WD) | 0.9600 |
| C(15)—H(15C) | 0.9600 | C(2W)—H(2WA) | 0.9600 |
| C(16)—H(16A) | 0.9600 | C(2W)—H(2WB) | 0.9600 |
| C(16)—H(16B) | 0.9600 | C(2W)—H(2WC) | 0.9600 |
| C(16)—H(16C) | 0.9600 | | |

TABLE 6

Single Crystal Diffraction Bond Angle of Crystal Form IV

| Angle | Value | Angle | Value |
|---|---|---|---|
| C(15)—N(1)—C(14) | 113.3(2) | C(3)—C(4)—C(7) | 120.0(2) |
| C(15)—N(1)—C(16) | 111.3(2) | C(6)—C(5)—C(4) | 121.5(2) |
| C(14)—N(1)—C(16) | 110.1(2) | C(6)—C(5)—H(5A) | 119.2 |
| C(15)—N(1)—H(1N) | 107.3 | C(4)—C(5)—H(5A) | 119.2 |
| C(14)—N(1)—H(1N) | 107.3 | C(1)—C(6)—C(5) | 118.8(2) |
| C(16)—N(1)—H(1N) | 107.3 | C(1)—C(6)—H(6A) | 120.6 |
| C(17)—O(1)—C(1) | 118.7(1) | C(5)—C(6)—H(6A) | 120.6 |
| C(8)—O(3)—H(3A) | 109.2(2) | C(4)—C(7)—C(14) | 113.1(1) |
| C(2)—C(1)—C(6) | 121.4(2) | C(4)—C(7)—C(8) | 112.1(1) |
| C(2)—C(1)—O(1) | 117.0(2) | C(14)—C(7)—C(8) | 109.7(1) |
| C(6)—C(1)—O(1) | 121.5(2) | C(4)—C(7)—H(7A) | 107.2 |
| C(1)—C(2)—C(3) | 119.1(2) | C(14)—C(7)—H(7A) | 107.2 |
| C(1)—C(2)—H(2A) | 120.4 | C(8)—C(7)—H(7A) | 107.2 |
| C(3)—C(2)—H(2A) | 120.4 | O(3)—C(8)—C(9) | 106.3(2) |
| C(2)—C(3)—C(4) | 121.1(2) | O(3)—C(8)—C(13) | 110.3(1) |
| C(2)—C(3)—H(3B) | 119.5 | C(9)—C(8)—C(13) | 109.1(2) |
| C(4)—C(3)—H(3B) | 119.5 | O(3)—C(8)—C(7) | 109.0(1) |
| C(5)—C(4)—C(3) | 118.0(2) | C(9)—C(8)—C(7) | 111.6(1) |
| C(5)—C(4)—C(7) | 121.9(2) | C(13)—C(8)—C(7) | 110.4(1) |
| C(10)—C(9)—C(8) | 112.8(2) | N(1)—C(15)—H(15C) | 109.5 |
| C(10)—C(9)—H(9A) | 109.0 | H(15A)—C(15)—H(15C) | 109.5 |
| C(8)—C(9)—H(9A) | 109.0 | H(15B)—C(15)—H(15C) | 109.5 |
| C(10)—C(9)—H(9B) | 109.0 | N(1)—C(16)—H(16A) | 109.5 |
| C(8)—C(9)—H(9B) | 109.0 | N(1)—C(16)—H(16B) | 109.5 |
| H(9A)—C(9)—H(9B) | 107.8 | H(16A)—C(16)—H(16B) | 109.5 |
| C(9)—C(10)—C(11) | 112.0(2) | N(1)—C(16)—H(16C) | 109.5 |
| C(9)—C(10)—H(10A) | 109.2 | H(16A)—C(16)—H(16C) | 109.5 |
| C(11)—C(10)—H(10A) | 109.2 | H(16B)—C(16)—H(16C) | 109.5 |
| C(9)—C(10)—H(10B) | 109.2 | O(2)—C(17)—O(1) | 123.3(2) |
| C(11)—C(10)—H(10B) | 109.2 | O(2)—C(17)—C(18) | 125.5(2) |
| H(10A)—C(10)—H(10B) | 107.9 | O(1)—C(17)—C(18) | 111.2(2) |
| C(12)—C(11)—C(10) | 110.0(2) | C(19)—C(18)—C(23) | 118.5(2) |
| C(12)—C(11)—H(11A) | 109.7 | C(19)—C(18)—C(17) | 122.8(2) |
| C(10)—C(11)—H(11A) | 109.7 | C(23)—C(18)—C(17) | 118.6(2) |
| C(12)—C(11)—H(11B) | 109.7 | C(18)—C(19)—C(20) | 120.4(2) |
| C(10)—C(11)—H(11B) | 109.7 | C(18)—C(19)—H(19A) | 119.8 |
| H(11A)—C(11)—H(11B) | 108.2 | C(20)—C(19)—H(19A) | 119.8 |
| C(13)—C(12)—C(11) | 110.3(2) | C(21)—C(20)—C(19) | 121.5(2) |
| C(13)—C(12)—H(12A) | 109.6 | C(21)—C(20)—H(20A) | 119.3 |
| C(11)—C(12)—H(12A) | 109.6 | C(19)—C(20)—H(20A) | 119.3 |
| C(13)—C(12)—H(12B) | 109.6 | C(20)—C(21)—C(22) | 117.7(2) |
| C(11)—C(12)—H(12B) | 109.6 | C(20)—C(21)—C(24) | 120.6(3) |
| H(12A)—C(12)—H(12B) | 108.1 | C(22)—C(21)—C(24) | 121.6(3) |
| C(12)—C(13)—C(8) | 112.9(2) | C(21)—C(22)—C(23) | 121.6(2) |
| C(12)—C(13)—H(13A) | 109.0 | C(21)—C(22)—H(22A) | 119.2 |
| C(8)—C(13)—H(13A) | 109.0 | C(23)—C(22)—H(22A) | 119.2 |
| C(12)—C(13)—H(13B) | 109.0 | C(18)—C(23)—C(22) | 120.3(2) |
| C(8)—C(13)—H(13B) | 109.0 | C(18)—C(23)—H(23A) | 119.8 |
| H(13A)—C(13)—H(13B) | 107.8 | C(22)—C(23)—H(23A) | 119.8 |
| N(1)—C(14)—C(7) | 114.2(2) | C(21)—C(24)—H(24A) | 109.5 |
| N(1)—C(14)—H(14A) | 108.7 | C(21)—C(24)—H(24B) | 109.5 |
| C(7)—C(14)—H(14A) | 108.7 | H(24A)—C(24)—H(24B) | 109.5 |

TABLE 6-continued

Single Crystal Diffraction Bond Angle of Crystal Form IV

| N(1)—C(14)—H(14B) | 108.7 | C(21)—C(24)—H(24C) | 109.5 |
| C(7)—C(14)—H(14B) | 108.7 | H(24A)—C(24)—H(24C) | 109.5 |
| H(14A)—C(14)—H(14B) | 107.6 | H(24B)—C(24)—H(24C) | 109.5 |
| N(1)—C(15)—H(15A) | 109.5 | O(1W)—S(1)—C(2W) | 110.9(3) |
| N(1)—C(15)—H(15B) | 109.5 | O(1W)—S(1)—C(1W) | 104.1(2) |
| H(15A)—C(15)—H(15B) | 109.5 | C(2W)—S(1)—C(1W) | 103.3(2) |

Figure 9:
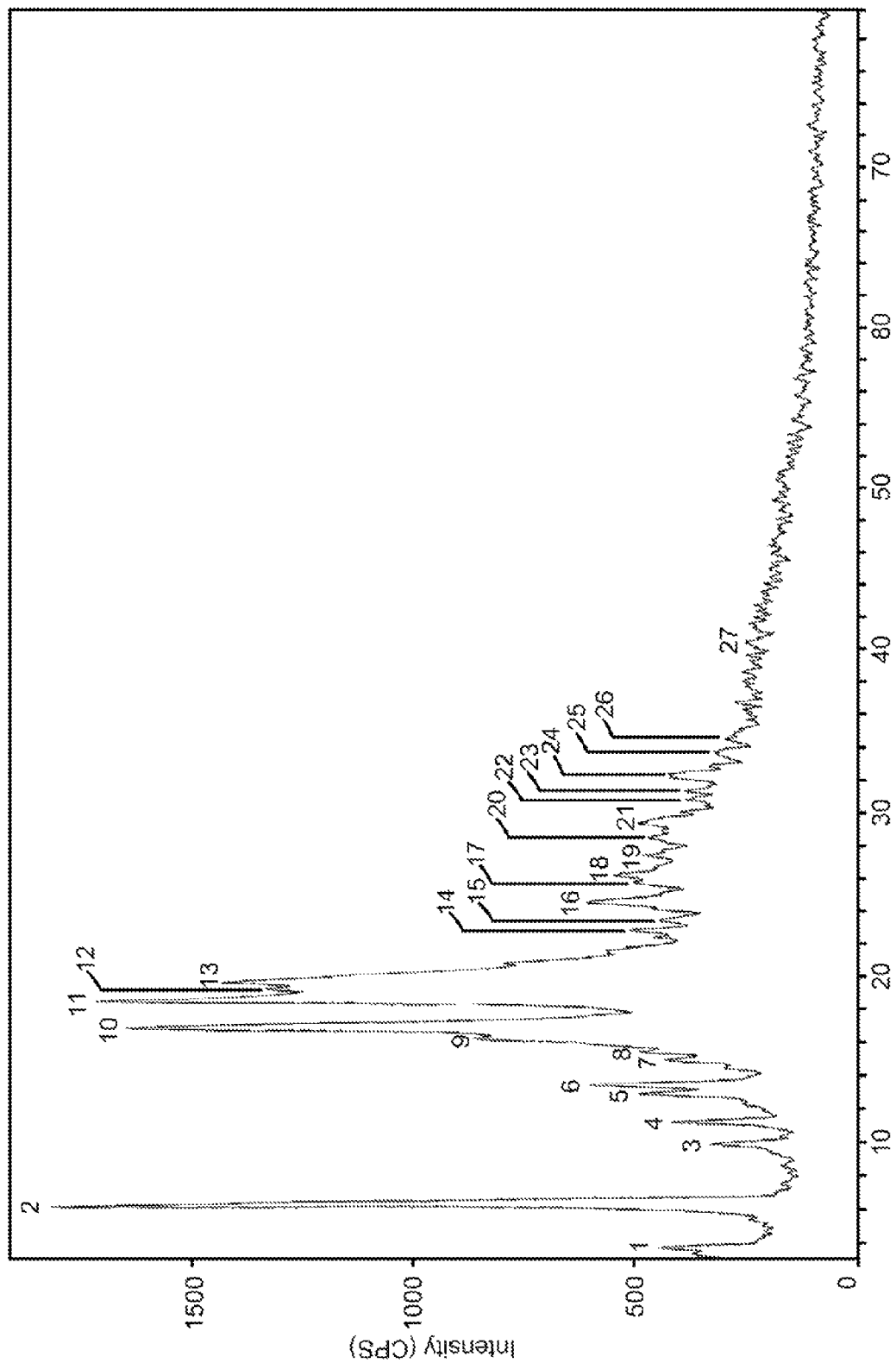
FIG. 9 is a powder X-ray diffractogram of a crystal form V.

Another object of the present disclosure is to provide a crystal form V of a compound of formula (I). The crystal form V exhibits a powder X-ray diffraction pattern obtained using CuK$_\alpha$ radiation and having characteristic peaks expressed in degrees 2θ (±0.2° 2θ) at 6.540, 13.541, 16.321, 17.200, 18.860, 19.520 and 19.940; preferably, exhibits a powder X-ray diffraction pattern having characteristic peaks expressed in degrees 2θ (±0.2° 2θ) at 3.801, 6.540, 9.941, 11.280, 13.039, 13.541, 16.321, 17.200, 18.860, 19.520, 19.940 and 24.660; more preferably, exhibits a powder X-ray diffraction pattern having characteristic peaks expressed in degrees 2θ (±0.2° 2θ) at 3.801, 6.540, 9.941, 11.280, 13.039, 13.541, 15.039, 15.534, 16.321, 17.200, 18.860, 19.520, 19.940, 22.901, 23.580, 24.660, 25.841, 26.320, 27.521, 28.598, 29.538, 30.880, 31.365, 32.421, 33.800 and 34.539; further preferably, exhibits a powder X-ray diffraction pattern substantially as shown in FIG. 9.

Figure 10:
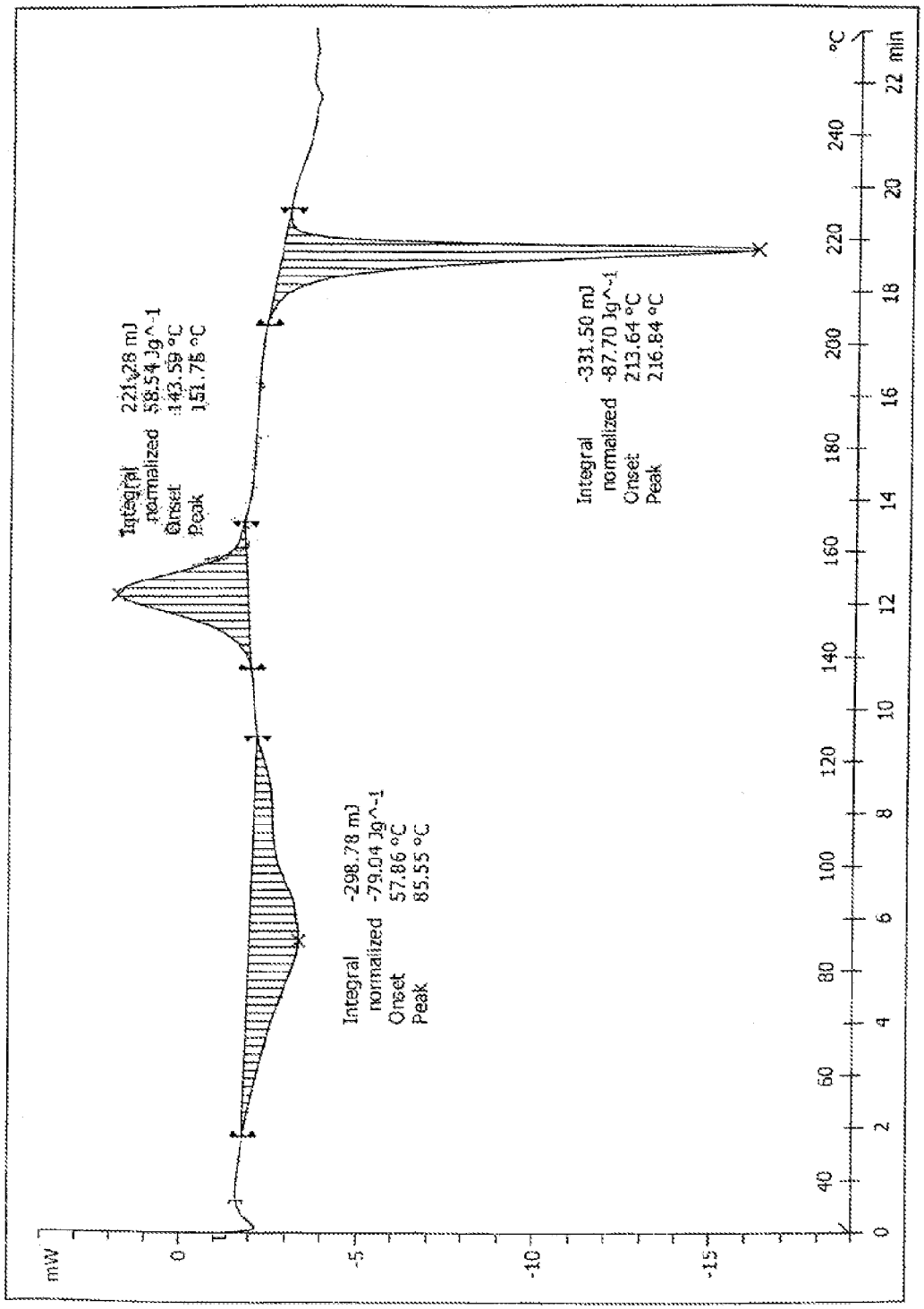
FIG. 10 is a DSC spectrum of a crystal form V.

In one preferred embodiment of the present disclosure, the crystal form V has a melting point of 211.8° C.-212.8° C. and a DSC spectrum substantially as shown in FIG. 10, which has two endothermic peaks at 86° C. and 217° C. respectively and an exothermic peak at 152° C.

As compared to the compound described in CN1955159A, crystal forms I, II, III, IV, and V of formula (I) (including its solvates) all exhibit higher and much narrower range of melting points.

According to conventional methods for manufacturing medicaments in the art, the crystal form I, the crystal form II, the crystal form III, the crystal form IV, and the crystal form V of 4-[2-dimethylamino-1-(1-hydroxycyclohexyl)ethyl]phenyl 4-methylbenzoate hydrochloride of the present disclosure may be made into suitable dosage forms, such as dosage forms for oral, injection, transdermal, nasal, mucosal and inhalation administration. The dosage forms for oral administration may be any one of tablets, capsules, soft capsules, drop pills, solutions, suspensions, emulsions and powders, or may be sustained release, site specific delivery, fast release, or orally disintegrating dosage forms. The dosage forms for injection administration may be dosage forms for intravenous, subcutaneous, intramuscular or intraperitoneal injection administration, may be solutions, suspensions or emulsions, and may also be normal dosage forms or long acting dosage forms such as implants, microspheres or gels. The dosage forms for transdermal administration may be transdermal patches, gels or other forms. The dosage forms for nasal and inhalation administration may be solutions, suspensions, emulsions or powders. The dosage forms for mucosal administration may be solutions, suspensions, emulsions, powders or suppositories.

The present disclosure further relates to a pharmaceutical composition comprising an effective amount of the crystal form I, the crystal form II, the crystal form III, the crystal form IV, or the crystal form V of 4-[2-dimethylamino-1-(1-hydroxycyclohexyl)ethyl]phenyl 4-methylbenzoate hydrochloride, and pharmaceutically acceptable carriers or diluents. The carriers may be any inert organics or inorganics, such as water, gelatin, cellulose and starch, and may also be other conventional additives, such as stabilizers, moistening agents, emulsifiers, flavoring agents and buffers.

Another object of the present disclosure is to provide use of the crystal form I, the crystal form II, the crystal form III, the crystal form IV or the crystal form V of the compound of formula (I) in the preparation of a medicament for treating diseases associated with 5-hydroxytryptamine (5-HT) and/or norepinephrine (NA) reuptake.

In one preferred embodiment of the present disclosure, the diseases associated with 5-hydroxytryptamine (5-HT) and/or norepinephrine (NA) reuptake are central nervous system diseases, preferably, depression, anxiety disorder, panic disorder, agoraphobia, post traumatic stress disorder, premenstrual dysphoric disorder, fibromyalgia, attention deficit disorder, obsessive-compulsive syndrome, autistic disorder, autism, schizophrenia, obesity, hyperorexia nervosa and anorexia nervosa, Tourette syndrome, vasomotor flushing, cocaine or alcohol addiction, sexual disturbance, borderline personality disorder, chronic fatigue syndrome, urinary incontinence, pain, Shy Drager syndrome, Raynaud syndrome, Parkinson's disease, or epilepsy. The daily dose may be within a range of 1 mg to 1000 mg per day by single or multiple daily administration.

Another embodiment provides a method for preparing the crystal form I of the compound of formula (I), comprising: dissolving 4-[2-dimethylamino-1-(1-hydroxycyclohexyl)ethyl]phenyl 4-methylbenzoate hydrochloride in a solvent; and recrystallizing 4-[2-dimethylamino-1-(1-hydroxycyclohexyl)ethyl]phenyl 4-methylbenzoate hydrochloride at 10° C.-70° C. under normal pressure or vacuum (−0.1 Mpa), wherein the solvent is any one or a mixture of any two solvents selected from the group of methanol, ethanol, n-propanol, isopropanol or n-butanol, chloroform, carbon tetrachloride, dichloroethane, DMF, dioxane, pyridine, ethyl acetate, acetonitrile, and petroleum ether, and wherein the volume ratio of the two solvents in the mixture is 1:10 to 10:1, and the ratio of the weight of 4-[2-dimethylamino-1-(1-hydroxycyclohexyl)ethyl]phenyl 4-methylbenzoate hydrochloride (mg) to the volume of the solvent (ml) is 100:1 to 4:1 or dissolving 4-[2-dimethylamino-1-(1-hydroxycyclohexyl)ethyl]phenyl 4-methylbenzoate hydrochloride in dichloromethane or acetonitrile and recrystallizing at 40° C.-60° C. under normal pressure; or maintaining 4-[2-dimethylamino-1-(1-hydroxycyclohexyl)ethyl]phenyl 4-methylbenzoate hydrochloride at 100° C.-150° C. in the absence of a solvent for 1-6 h.

Another embodiment of the present disclosure provides a method for preparing the crystal form II of the compound of formula (I), comprising: dissolving 4-[2-dimethylamino-1-(1-hydroxycyclohexyl)ethyl]phenyl 4-methylbenzoate hydrochloride in water; and recrystallizing 4-[2-dimethylamino-1-(1-hydroxycyclohexyl)ethyl]phenyl 4-methylbenzoate hydrochloride at 25° C.-40° C.; or dissolving 4-[2-dimethylamino-1-(1-hydroxycyclohexyl)ethyl]phenyl 4-methylbenzoate hydrochloride in acetonitrile and recrystallizing 4-[2-dimethylamino-1-(1-hydroxycyclohexyl) ethyl]phenyl 4-methylbenzoate hydrochloride at 25° C., wherein the ratio of the weight of 4-[2-dimethylamino-1-(1-hydroxycyclohexyl)ethyl]phenyl 4-methylbenzoate hydrochloride (mg) to the volume of the solvent (ml) is 10:1 to 20:1; or placing 4-[2-dimethylamino-1-(1-hydroxycyclohexyl) ethyl]phenyl 4-methylbenzoate hydrochloride at 25° C. under a humidity of 75%-92.5% in the absence of a solvent for 5-10 days.

Another embodiment provides a method for preparing the crystal form III of the compound of formula (I), comprising: dissolving 4-[2-dimethylamino-1-(1-hydroxycyclohexyl) ethyl]phenyl 4-methylbenzoate hydrochloride in dichloromethane or chloroform; and recrystallizing 4-[2-dimethylamino-1-(1-hydroxycyclohexyl)ethyl]phenyl 4-methylbenzoate hydrochloride at 50° C. under vacuum (−0.09 Mpa), wherein the ratio of the weight of 4-[2-dimethylamino-1-(1-hydroxycyclohexyl)ethyl]phenyl 4-methylbenzoate hydrochloride (mg) to the volume of the solvent (ml) is 20:1 to 25:1; or heating 4-[2-dimethylamino-1-(1-hydroxycyclohexyl)ethyl]phenyl 4-methylbenzoate hydrochloride at a temperature of 115° C. in the absence of a solvent for a period of time, e.g., 8 minutes; or physical disrupting the molecular lattice of 4-[2-dimethylamino-1-(1-hydroxycyclohexyl)ethyl]phenyl 4-methylbenzoate hydrochloride.

A further embodiment of the present disclosure provides a method for preparing the crystal form IV of the compound of formula (I), comprising: dissolving 4-[2-dimethylamino-1-(1-hydroxycyclohexyl)ethyl]phenyl 4-methylbenzoate hydrochloride in a mixed solvent of dimethyl sulfoxide and ethyl acetate; and recrystallizing 4-[2-dimethylamino-1-(1-hydroxycyclohexyl)ethyl]phenyl 4-methylbenzoate hydrochloride at 18° C., wherein the ratio of the weight of 4-[2-dimethylamino-1-(1-hydroxycyclohexyl)ethyl]phenyl 4-methylbenzoate hydrochloride (mg) to the volume of the solvent (ml) is 10:1 to 15:1, and the volume ratio of dimethyl sulfoxide to ethyl acetate is 1:10.

Another embodiment of the present disclosure is to provide a method for preparing the crystal form V of the compound of formula (I), comprising: dissolving 4-[2-dimethylamino-1-(1-hydroxycyclohexyl)ethyl]phenyl 4-methylbenzoate hydrochloride in a mixed solvent of chloroform and petroleum ether or a mixed solvent of dichloromethane and petroleum ether; and recrystallizing 4-[2-dimethylamino-1-(1-hydroxycyclohexyl)ethyl]phenyl 4-methylbenzoate hydrochloride at 18° C., wherein the ratio of the weight of 4-[2-dimethylamino-1-(1-hydroxycyclohexyl)ethyl]phenyl 4-methylbenzoate hydrochloride (mg) to the volume of the solvent (ml) is 9:1 to 20:1, and the volume ratio of chloroform to petroleum ether or the volume ratio of dichloromethane to petroleum ether is 1:10.

The method for testing the crystal forms of the present disclosure comprises the following tests.

1. Single crystal X-ray Diffraction Test
    1) Test instrument: Rigaku MicroMax 002+ single crystal diffractometer.
    2) Test conditions: $CuK_\alpha$ radiation, confocal monochromator, diameter of collimator is Φ=0.30 mm, distance between crystal and the detector is d=50 mm, tube voltage is 45 KV, tube current is 0.88 mA, scanning mode is ω and κ.
2. Powder X-ray Diffraction Test
    1) Sample treatment: the sample is ground and passes through a 100-mesh sieve, and 50 mg of the sieved sample is used.
    2) Test instrument: Japan Rigaku D/max-2550 Powder X-ray diffractometer.
    3) Test conditions: $CuK_\alpha$ radiation, graphite monochromator, a tube voltage of 40 KV, a tube current of 150 mA, a 2θ scanning range of 3-80°, a scanning speed of 8° C./min, and a step of 0.02°. Slit conditions: a divergence slit of 1°, a height limiting slit of 10 mm, an anti-scatter slit of 1°, and a receiving slit of 0.15 mm.
3. Melting point test
    1) Test instrument: WRS-1B digital melting point apparatus available from Shanghai Suoguang Light & Electricity Technology. Co., Ltd.
    2) Test conditions:
        the crystal form I, an initial temperature of 200° C. and a heating rate of 1° C./min.
        the crystal form II, an initial temperature of 80° C. and a heating rate of 1° C./min.
        the crystal form III, an initial temperature of 80° C. and a heating rate of 1° C./min.
        the crystal form IV, an initial temperature of 80° C. and a heating rate of 1° C./min.
        the crystal form V, an initial temperature of 60° C. and a heating rate of 1° C./min.
4. DSC (differential scanning calorimetry) test, test conditions: Switzerland DSC1 thermal analyzer, an initial temperature set to 30° C., a final temperature set to 260° C., and a heating rate set to 10K/min.

As discussed in the background, compound 4-[2-dimethylamino-1-(1-hydroxycyclohexyl)ethyl]phenyl 4-methylbenzoate hydrochloride can be obtained as a white crystalline solid with a melting point of 203.2° C.-206.5° C. The same compound, when recrystallized in accordance with the various embodiments described herein, give rise to crystal forms I-V, which are demonstrated to have different properties. In particular, one or more of the crystal forms I, II, III, IV and V of the compound (including its solvates) exhibit much enhanced stability and bioavailability as compared to the compound in a crystal form that corresponds to a melting point of 203.2° C.-206.5° C.

The following examples describe the present disclosure in more detail. These examples shall not be construed to limit the present disclosure.

EXAMPLE 1

Preparation of Compound of Formula (I)

10 g of desmethyl-venlafaxine (compound III) was dissolved in 200 ml of anhydrous pyridine, and cooled to 0° C. Equimolar 4-Methylbenzoyl chloride dissolved in anhydrous tetrahydrofuran was added dropwise, and reaction was conducted at this temperature under stirring for 5 hours. Then, most of solvent was removed by vacuum evaporation. The residue was poured into 400 ml of water, adjusted under stirring until pH was 9, and stored overnight. The precipitated solid was filtered out, washed with water for three times, and dried to obtain a crude product. The crude product was recrystallized with 80 ml of anhydrous ethanol/ethyl acetate (1:1) to obtain 8.0 g of white solid with a melting point of 159.0° C.-162.2° C. and a yield of 55.2%.

20 ml of anhydrous ethanol was added to 2.0 g of the above product, and concentrated hydrochloric acid was added dropwise until the product was dissolved completely. After the solvent was removed by vacuum evaporation, 20 ml of ethyl acetate was added to the residue under stirring. The precipitated solid was filtered out to obtain 2.0 g of white crystalline solid with a melting point of 203.2° C.-206.5° C. This melting point agrees with the result in CN1955159A.

EXAMPLE 2

Preparation of Crystal Form I 500 mg of the compound of formula (I) was recrystallized in a mixed solvent of 3 ml of ethanol and 30 ml of ethyl acetate at 18° C. for 1 day to obtain the crystal form I as a colorless transparent needle-like crystal.

The melting point of the crystal form I is 213.0° C.-213.8° C., the powder X-ray diffractogram of the crystal form I is shown in FIG. 1, and the DSC spectrum of the crystal form I is shown in FIG. 2.

In addition, as determined by the powder X-ray diffraction, the crystal obtained according to conditions in Table 7 is also the crystal form I.

TABLE 7

Preparation of Crystal Form I

| No. | Sample Weight (mg) | Solvent | Solvent Volume (ml) | Treatment Conditions |
|---|---|---|---|---|
| 1 | 50 | dichloromethane | 1.4 | 60° C. |
| 2 | 50 | acetonitrile | 3.2 | 60° C. |
| 3 | 50 | DMF | 0.6 | 60° C. |
| 4 | 50 | dioxane | 2.4 | 60° C. |
| 5 | 50 | ethanol | 0.5 | 60° C. |
| 6 | 50 | isopropanol | 0.8 | 60° C. |
| 7 | 50 | n-propanol | 0.6 | 60° C. |
| 8 | 50 | n-butanol | 0.6 | 60° C. |
| 9 | 50 | dichloromethane | 1.4 | 40° C. |
| 10 | 50 | acetonitrile | 3.2 | 40° C. |
| 11 | 50 | DMF | 0.6 | 40° C. |
| 12 | 50 | dioxane | 2.4 | 40° C. |
| 13 | 50 | n-propanol | 0.6 | 40° C. |
| 14 | 50 | n-butanol | 0.6 | 40° C. |
| 15 | 50 | pyridine | 0.8 | 40° C. |
| 16 | 50 | dichloromethane | 1.4 | 25° C. |
| 17 | 50 | n-propanol | 0.6 | 25° C. |
| 18 | 300 | methanol | 10 | 50° C., vacuum: −0.1 Mpa |
| 19 | 300 | n-butanol | 14 | 70° C., vacuum: −0.1 Mpa |
| 20 | 300 | acetonitrile | 25 | 50° C., vacuum: −0.1 Mpa |
| 21 | 300 | pyridine | 10 | 50° C., vacuum: −0.1 Mpa |
| 22 | 300 | dioxane | 50 | 50° C., vacuum: −0.1 Mpa |
| 23 | 500 | isopropanol:petroleum ether | 8:80 | 18° C., precipitation method |
| 24 | 500 | DMF:ethyl acetate | 4:40 | 18° C., precipitation method |
| 25 | 500 | acetonitrile:ethyl acetate | 10:100 | 18° C., precipitation method |
| 26 | 500 | ethanol:ethyl acetate | 3:30 | 18° C., precipitation method |
| 27 | 200 | pyridine:ethyl acetate | 5:50 | 18° C., precipitation method |
| 28 | 200 | — | — | 105° C., 4 h |
| 29 | 200 | — | — | 105° C., 6 h |
| 30 | 200 | — | — | 115° C., 2 h |
| 31 | 200 | — | — | 115° C., 4 h |
| 32 | 200 | — | — | 140° C., 1 h |

EXAMPLE 3

Preparation of Crystal Form II 50 mg of the compound of formula (I) was recrystallized in 3.2 ml of acetonitrile at 22° C. for 15 days to obtain the crystal form II as a colorless transparent columnar crystal.

The melting point of the crystal form II is 209.5° C.-210.2° C., the powder X-ray diffractogram of the crystal form II is shown in FIG. 3, and the DSC spectrum of the crystal form II is shown in FIG. 4.

In addition, as determined by the powder X-ray diffraction, the crystal obtained according to conditions in Table 8 is also the crystal form II.

TABLE 8

Preparation of Crystal Form II

| No. | Sample Weight (mg) | Solvent | Solvent Volume (ml) | Physical Conditions |
|---|---|---|---|---|
| 1 | 50 | water | 4.5 | 40° C. |
| 2 | 50 | water | 4.5 | 25° C. |
| 3 | 300 | — | — | 25° C., humidity: 92.5%, 5 days |

EXAMPLE 4

Preparation of Crystal Form III 300 mg of the compound of formula (I) was recrystallized in 14 ml of chloroform at 50° C. under vacuum, and the solvent was removed rapidly to obtain the crystal form III as a white powder solid.

The melting point of the crystal form III is 210.1-211.9° C., the powder X-ray diffractogram of the crystal form III is shown in FIG. 5, and the DSC spectrum of the crystal form III is shown in FIG. 6.

In addition, as determined by the melting point test and the DSC, the crystal obtained according to conditions in Table 9 is also the crystal form III.

TABLE 9

Preparation of Crystal Form III

| No. | Sample Weight (mg) | Solvent | Solvent Volume (ml) | Physical Conditions |
|---|---|---|---|---|
| 1 | 300 | dichloromethane | 15 | 50° C., vacuum: −0.09 Mpa |
| 2 | 3000 | — | — | physical disruption of the molecular lattice |
| 3 | 50 | — | — | 115° C., 8 min |

EXAMPLE 5

Preparation of Crystal Form IV 500 mg of the compound of formula (I) was recrystallized in a mixed solvent of 4 ml of DMSO and 40 ml of ethyl acetate at 18° C. for 1 day to obtain the crystal form IV as a colorless transparent lump-like crystal.

The powder X-ray diffractogram of the crystal form IV is shown in FIG. 7, the melting point of the crystal form IV is 213.2° C.-213.9° C., and the DSC spectrum of the crystal form IV is shown in FIG. 8.

EXAMPLE 6

Preparation of Crystal Form V 500 mg of the compound of formula (I) was recrystallized in a mixed solvent of 5 ml of chloroform and 50 ml of petroleum ether at 18° C., and solid was precipitated rapidly to obtain the crystal form V as a white powder solid.

The powder X-ray diffractogram of the crystal form V is shown in FIG. 9, the melting point of the crystal form V is 211.8° C.-212.8° C., and the DSC spectrum of the crystal form V is shown in FIG. 10.

In addition, the crystal form V may also be obtained by recrystallizing the compound of formula (I) in a mixed solvent of dichloromethane and petroleum ether with a volume ratio of 1:10 at 18° C. using the precipitation method.

EXAMPLE 7

Stability Test During the Process of the Preparation of Compound of Formula (I) and Crystal Form II of Compound of Formula (I)

Figure 17:
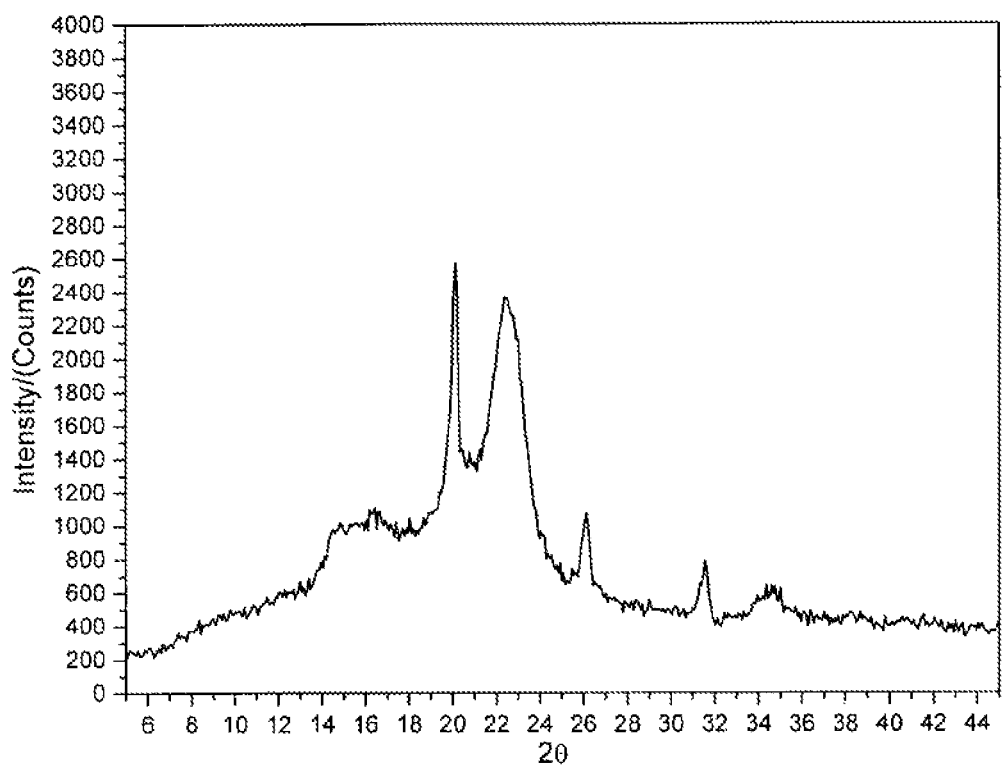
FIG. 17 is a powder X-ray diffractogram of blank excipients.

1. Test Instrument
High-speed wet granulator Beijing Aeronautical manufacturing Technology Research Institute HLSH2-6A
8 Dies rotating presser Shanghai Tianxiang & Chentai Pharmaceutical Machinery Co., Ltd.
Powder X-ray diffraction SHIMADZU, Japan, XRD-7000
2. Test Materials
  (1) Raw Materials
Compound of Formula (I) Prepared according to the method in Example 1
Crystal Form II Prepared according to the method in Example 3
  (2) Excipients
Hydroxypropyl Methyl Cellulose K4M Dow Chemical, US (batch No. WK19012NO2)
Microcrystalline Cellulose (batch No. FMC, US C1006066-S)
Povidone K30 (batch No. 05400111258) ISP, US
Magnesium Stearate (batch No. 20091011) Hunan ER-KANG Pharmaceutical Co., Ltd.
3. Test Method The raw material and the excipients were weighed according to the formulation. Dry granulation tabletting method and wet granulation tabletting method were used to prepare the tablets of compound of Formula (I) and the crystal form II of compound of Formula (I) respectively, powder X-ray diffraction method was used to monitor the crystal transition of the raw material in mixed powder, dry granules, and tablets. The mixed excipients powder was prepared without raw material and magnesium stearate (blank excipients) according to the formulation of tablets, and used powder X-ray diffraction method to monitor the blank excipients. The powder X-ray diffractogram of the blank excipients is shown in FIG. 17.

(1) Wet Granulation Tabletting Method

Formulation: 25 g of the Compound of Formula (I) or the Crystal Form II of compound of Formula (I) (calculated based on anhydrous substance), 75 g of HPMC K4M CR, 150 g of microcrystalline cellulose, appropriate amount of 5% PVP ethanol solution, and 2.5 g magnesium stearate.

Preparation Method:

All of the excipients were dried at 80° C. until the loss on drying was less than 3%, and passed through a 80-mesh sieve for spare use. The compound of Formula (I) and the crystal form II of compound of Formula (I) were passed through a 80-mesh sieve for spare use;

The above raw material and excipients were weighed according to the formulation (except the magnesium stearate), placed in a high speed wet granulator, and premixed for 4 minutes to get the mixed powder;

An appropriate amount of the 5% PVP K30 ethanol solution was added to the mixed powder, which was then granulated, and dried under forced air at 60° C., until the loss on drying was less than 4%, and then the dry granules was obtained after granulation.

The dry granules were mixed with the magnesium stearate according to the formulation quantity, to obtain tablets after compressing. The tablet weight was 250 mg±15 mg, and the hardness was 6±1 kg.

(2) Dry Granulation Tabletting Method

Formulation: 25 g of the Compound of Formula (I) or the Crystal Form II of compound of Formula (I) (calculated based on anhydrous substance), 75 g of HPMC K4M CR, 150 g of microcrystalline cellulose, and 2.5 g magnesium stearate.

Preparation Method:

All the excipients were dried at 80° C. until the loss on drying was less than 3%, and passed through a 80-mesh sieve for spare use. And the compound of Formula (I) and the crystal form II of compound of Formula (I) were passed through a 80-mesh sieve for spare use;

The above raw material and excipients were weighed according to the formulation (except the magnesium stearate), mixed by equivalent addition method, then passed through a 60-mesh sieve for three times, and mixed well to get the mixed powder;

18 mm dies were used to produce big tablets, with the hardness of 1 kg-2 kg. The big tablets were crushed, and granulated to get the dry granules.

The dry granules was mixed with the magnesium stearate according to the formulation quantity, to obtain tablets after tablatting. The tablet weight was 250 mg±15 mg, and the hardness was 6±1 kg.

4. Test Results (1) Wet Granulation Tabletting Method

Figure 18:
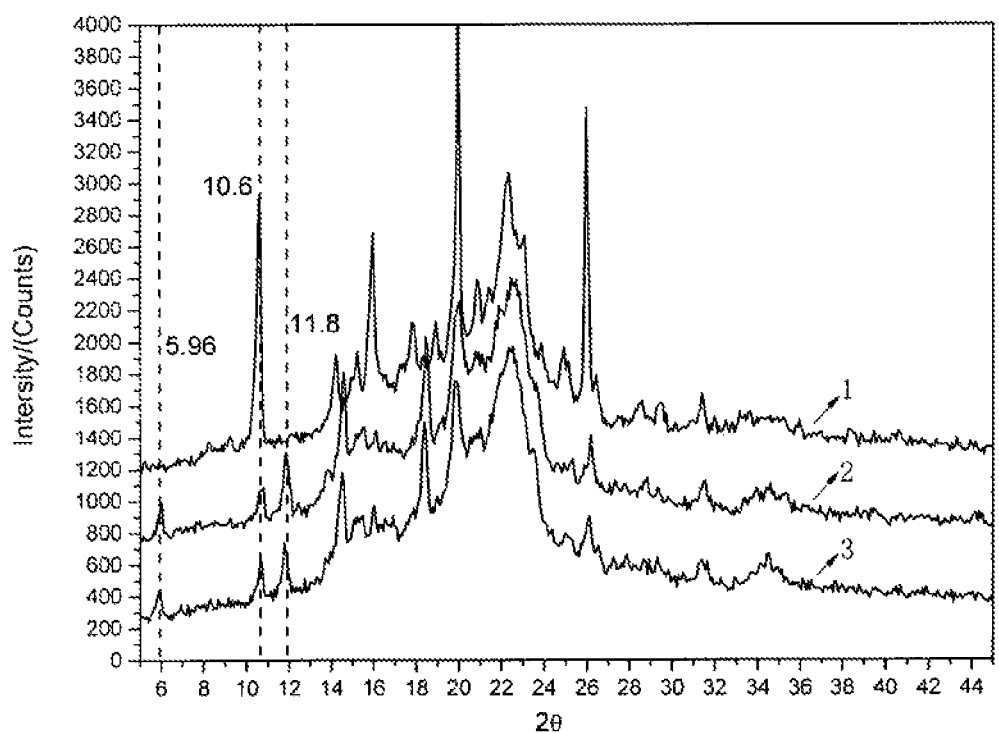
FIG. 18 is a powder X-ray diffractogram of compound of Formula (I) during the wet granulation tabletting process, wherein 1 is mixed powder, 2 is dry granules, and 3 is tablets.

The powder X-ray diffractogram of the Compound of Formula (I) during the wet granulation tabletting process is shown in FIG. 18.

Figure 19:
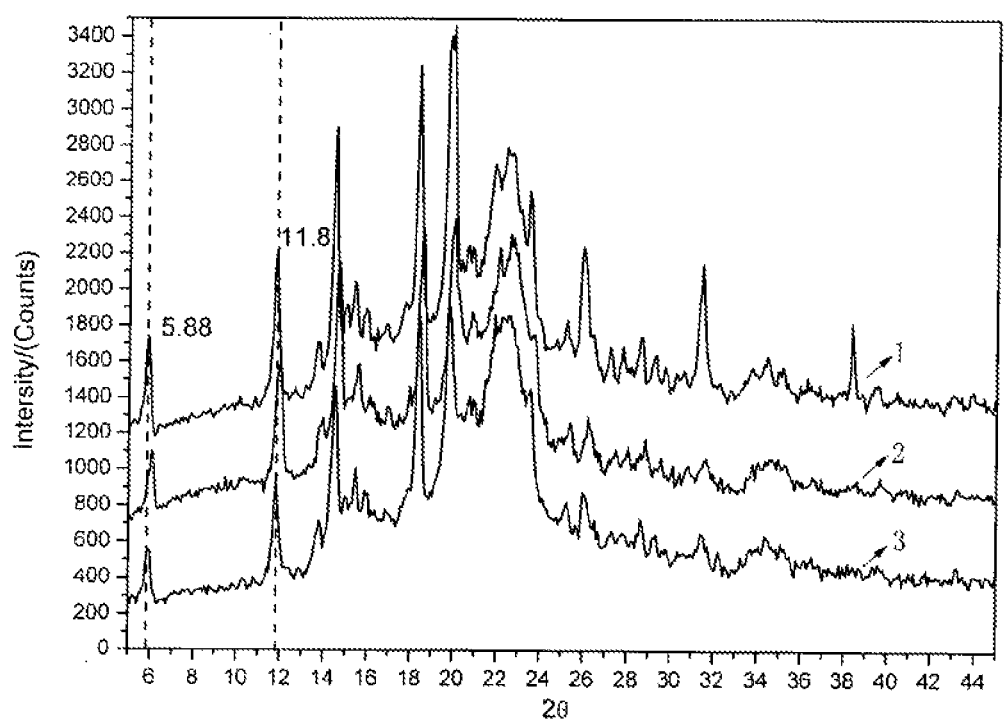
FIG. 19 is a powder X-ray diffractogram of a crystal form II of compound of Formula (I) during the wet granulation tabletting process, wherein 1 is mixed powder, 2 is dry granules, and 3 is tablets.

The powder X-ray diffractogram of the Crystal form II of compound of Formula (I) during the wet granulation tabletting process is shown in FIG. 19.

Results: It may be seen from the powder X-ray diffractogram of the excipients that, when 2θ<14, the excipients did not interfere with the detection of the raw material, consequently, the characteristic peak at 2θ<14 was chosen to monitor and evaluate the crystal form of the raw material. During the wet granulation tabletting process, the characteristic peaks of the compound of Formula (I) expressed in degrees 2θ at 5.9, 10.6 and 11.8 changed significantly at the preparation phases of mixed powder, dry granules, and tablets, which means the compound of Formula (I) is not stable during the preparation process. During the wet granulation tabletting process, the characteristic peaks of the Crystal Form II of compound of Formula (I) expressed in degrees 2θ at 5.9 and 11.8 have no changes at the preparation phases of mixed powder, dry granules, and tablets, which means the Crystal form II is stable during the preparation process.

(2) Dry Granulation Tabletting Method

Figure 20:
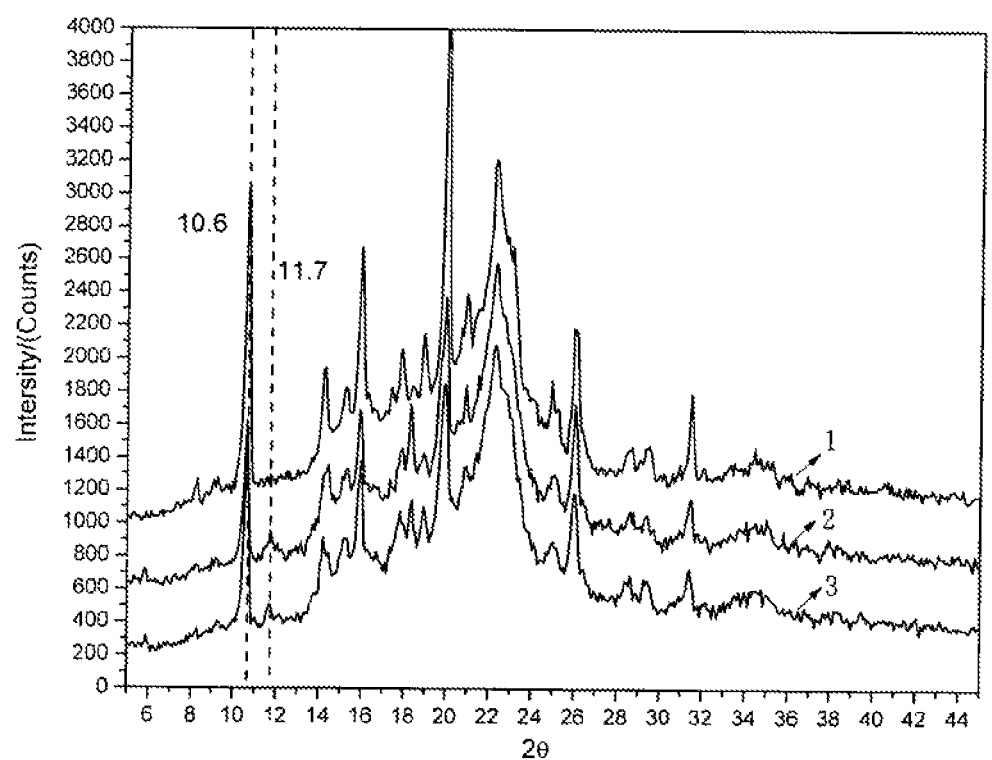
FIG. 20 is a powder X-ray diffractogram of compound of Formula (I) during the dry granulation tabletting process, wherein 1 is mixed powder, 2 is dry granules, and 3 is tablets.

The powder X-ray diffractogram of the Compound of Formula (I) during the dry granulation tabletting process is shown in FIG. 20.

Figure 21:
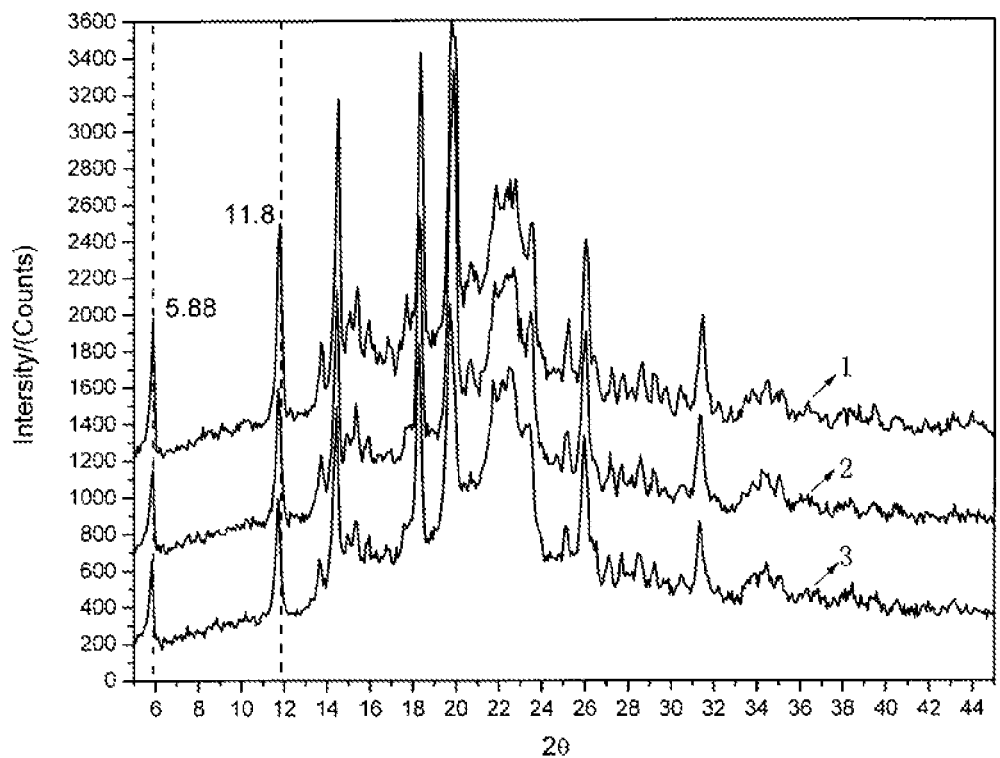
FIG. 21 is a powder X-ray diffractogram of a crystal form II of compound of Formula (I) during the dry granulation tabletting process, wherein 1 is mixed powder, 2 is dry granules, and 3 is tablets.

The powder X-ray diffractogram of the Crystal form II of compound of Formula (I) during the dry granulation tabletting process is shown in FIG. 21.

Results: It may be seen from the powder X-ray diffractogram of the excipients that, when 2θ<14, the excipients were not interfere with the monitor of the raw material, consequently, the characteristic peak at 2θ<14 was chosen to monitor and evaluate the crystal form of the raw material. During the dry granulation tabletting process, the characteristic peaks of the compound of Formula (I) expressed in degrees 2θ at 10.6 and 11.7 have changes at the preparation phases of mixed powder, dry granules, and tablets, which means the physical properties of the compound of Formula (I) is not stable during the preparation process. During the dry granulation tabletting process, the characteristic peaks of the crystal form II of compound of Formula (I) expressed in degrees 2θ at 5.9, 11.8 have no changes at the preparation phases of mixed powder, dry granules, and tablets, which means the crystal form II is stable during the preparation process.

EXAMPLE 8

Pharmacokinetics and Bioavailability Study of the Compound of Formula (I) and the Crystal Form I, the Crystal Form II and the Crystal Form III of Compound of Formula (I) in Rats 1. Instrument and Equipment API 4000 Triple Quadrupole Mass Spectrometer, with an ion spray ionization source and an Analyst 1.4.1 data processing software, US, Applied Biosystem company.

Agilent 1200 HPLC system, including binary infusion pump, autosampler, column heater, and switching valve, US, Aglient company; The column is Agilent Eclispe XDB C18 column (50×4.6 mm, 1.8 μm).

L-128 Sample concentrator, Beijing Laiheng Scientific Co. Ltd Co., Ltd

2. Reagent and Material n-Hexane (analytical reagent) China National Medicines Corporation Ltd.
Dichloromethane (analytical reagent) Tianjin Fuchen Chemical Reagent Factory
Ammonium acetate (batch No. 431311, Aldrich 99.99+%)
Acetic acid (batch No. 45727, ≥99%) Fluka
Methanol (chromatographic grade, batch Merk No. 1422107813)

3. Test Drug

CMCNa suspension of the Compound of Formula (I) (prepared according to the method in Example 1)

CMCNa suspension of the Crystal form I (prepared according to the method in Example 2)

CMCNa suspension of the Crystal form II (prepared according to the method in Example 3)

CMCNa suspension of the Crystal form III (prepared according to the method in Example 4)

4. Animal

24 SD Rats, half male and half female, weight 200-260 g., provided by the animal center of Shandong Luye Pharmaceutical Co., Ltd., Certificate No. SYXK-20090013.

5. Method

Rats were randomly divided into four groups (6 rats/group) to receive a oral dose of Compound of Formula (I), Crystal Form I, Crystal Form II, and Crystal Form III at 4.5 mg/kg. Blood samples (0.40 mL) were collected via the ophthalmic vein at 0 (to serve as a control), 5 min, 0.25 h, 0.5 h, 1 h, 2 h, 3 h, 4 h, 6 h, 8 h, 10 h, 12 h, 24 h. After centrifugation (10 min, 10000 rpm) of blood samples, plasma samples were collected and stored at −35° C. until analysis.

6. Results

Figure 22:
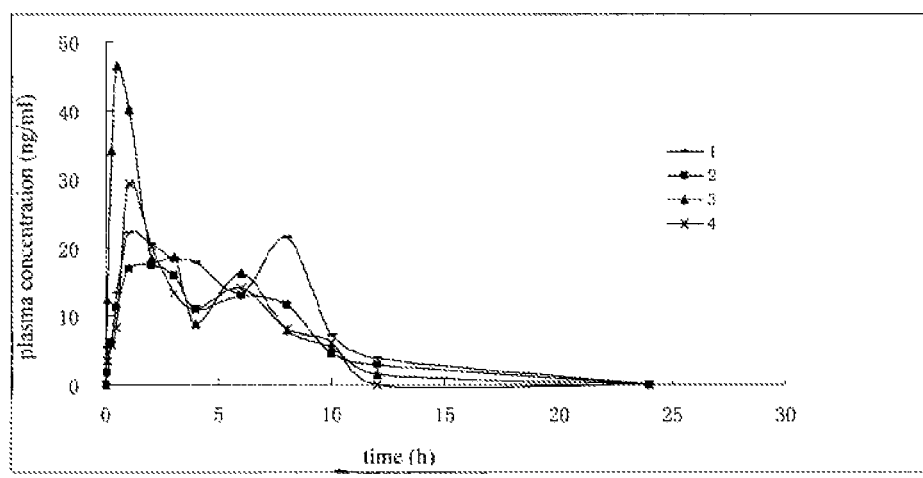
FIG. 22 shows the rat in vivo concentration-time curve of the groups of the crystal form I, the crystal form II and the crystal form III of compound of Formula (I), wherein 1 is the crystal form I, 2 is the crystal form II, 3 is the crystal form III, and 4 is the compound of Formula (I).

The plasma concentration-time curve of the groups of the compound of Formula (I), the crystal form I, the crystal form II and the crystal form III in rats are shown in FIG. 22.

The rat in vivo pharmacokinetic parameters of the groups of the compound of Formula (I), the crystal form I, the crystal form II and the crystal form III are shown in Table 10.

TABLE 10

The pharmacokinetic parameters and relative bioavailability of Formula (I), the crystal form I, the crystal form II and the crystal form III.

| Parameters | Unit | Crystal Form I | Crystal Form II | Crystal Form III | Compound of Formula (I)* |
|---|---|---|---|---|---|
| Melting points | ° C. | 213.0-213.8 | 209.5-210.2 | 209.5-212.6 | 203.2-206.5 |
| AUC (0-t) | ug/L * h | 194 | 130 | 187 | 138 |
| AUC (0-∞) | ug/L * h | 237 | 138 | 197 | 150 |
| MRT (0-t) | h | 5.20 | 4.95 | 3.69 | 4.86 |
| MRT (0-∞) | h | 8.13 | 5.60 | 4.36 | 5.33 |
| t½z | h | 4.68 | 2.38 | 2.83 | 2.59 |
| Tmax | h | 2.75 | 3.5 | 0.54 | 2.77 |
| CLz | L/h/kg | 7.28 | 11.37 | 9.08 | 10.68 |
| Vz | L/kg | 43.0 | 38.5 | 38.3 | 40.1 |
| Cmax | ug/L | 32.5 | 23.3 | 59.7 | 25.9 |
| Relative bioavailability | (%) | 141* | 94 | 135* | 100 |

*P < 0.05
*Compound of Formula (I) without recrystallization.

When the rats were isodose administrated by CMCNa suspension of the Compound of Formula (I), the Crystal Form I, the Crystal Form II, and the Crystal Form III, the relative bioavailability of the Crystal Form I, the Crystal Form II, and the Crystal Form III were 141%, 94%, and 135% in rats, respectively. The bioavailability of the Crystal Form II is equivalent to the compound of Formula (I), there was no significant difference between them (p>0.05). However, the bioavailability of the Crystal Form I and the Crystal Form III is better than the compound of Formula (I) and have significant difference as compared with the compound of Formula (I) (p<0.05), The results demonstrated that different crystal forms of the compound of Formula (I) have different absorption in vivo.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A crystal form III of [4-[2-dimethylamino-1-(1-hydroxycyclohexyl)ethyl]phenyl 4-methylbenzoate hydrochloride] exhibiting a powder X-ray diffraction pattern obtained using CuKα radiation and having characteristic peaks expressed in degrees 2θ(±0.2° 2θ) at 18.840, and exhibiting a powder X-ray diffraction pattern as shown in FIG. 5.

2. The crystal form III according to claim 1, having a melting point of 210.1-211.9° C.

3. The crystal form III according to claim 1 exhibiting a DSC (differential scanning calorimetry) spectrum as shown in FIG. 6.

4. A pharmaceutical composition comprising the crystal from III of [4-[2-dimethylamino-1-(1-hydroxycyclohexyl) ethyl]phenyl 4-methylbenzoate hydrochloride] of claim 1 and a pharmaceutically acceptable carrier.

5. A method for preparing the crystal form III of [4-[2-dimethylamino-1-(1-hydroxycyclohexyl)ethyl]phenyl 4-methylbenzoate hydrochloride] of claim 1, comprising:

dissolving 4-[2-dimethylamino-1-(1-hydroxycyclohexyl) ethyl]phenyl 4-methylbenzoate hydrochloride in dichloromethane or chloroform; and recrystallizing 4-[2-dimethylamino-1-(1-hydroxycyclohexyl)ethyl]phenyl 4-methylbenzoate hydrochloride at 50° C. under vacuum, wherein a ratio of the weight of 4-[2-dimethylamino-1-(1-hydroxycyclohexyl)ethyl] phenyl 4-methylbenzoate hydrochloride (mg) to the volume of the solvent (ml) is 20:1 to 25:1.

6. A method for preparing the crystal form III of [4-[2-dimethylamino-1-(1-hydroxycyclohexyl)ethyl]phenyl 4-methylbenzoate hydrochloride] of claim 1, comprising: heating 4-[2-dimethylamino-1-(1-hydroxycyclohexyl)ethyl]phenyl 4-methylbenzoate hydrochloride at a temperature of 115° C. in the absence of a solvent.

7. A crystal form III of [4-[2-dimethylamino-1-(1-hydroxycyclohexyl)ethyl]phenyl 4-methylbenzoate hydrochloride] exhibiting a powder X-ray diffraction pattern obtained using CuKα radiation and having characteristic peaks expressed in degrees 2θ (±0.2° 2θ) at 18.840 and exhibiting a DSC (differential scanning calorimetry) spectrum as shown in FIG. 6.

8. A pharmaceutical composition comprising the crystal from III of [4[2-dimethylamino-1-(1-hydroxycyclohexyl) ethyl]phenyl 4-methylbenzoate hydrochloride] of claim 7 and a pharmaceutically acceptable carrier.

* * * * *